(12) United States Patent
Smith et al.

(10) Patent No.: US 9,416,185 B2
(45) Date of Patent: Aug. 16, 2016

(54) HUMANIZED ANTIBODIES AGAINST TL1A

(71) Applicant: TEVA Biopharmaceuticals USA, Inc., Rockville, MD (US)

(72) Inventors: Rodger Smith, Jefferson, MD (US); Palanisamy Kanakaraj, Germantown, MD (US); Viktor Roschke, Bethesda, MD (US); Craig Rosen, Pasadena, MD (US); Bridget A. Cooksey, Macquarie Park (AU)

(73) Assignee: TEVA BIOPHARMACEUTICALS USA, INC., Rockville, MD (US)

( * ) Notice: Subject to any disclaimer, the term of this patent is extended or adjusted under 35 U.S.C. 154(b) by 23 days.

(21) Appl. No.: 14/244,603

(22) Filed: Apr. 3, 2014

(65) Prior Publication Data
US 2014/0315250 A1 Oct. 23, 2014

Related U.S. Application Data

(62) Division of application No. 13/585,792, filed on Aug. 14, 2012, now Pat. No. 8,728,482, which is a division of application No. 12/270,673, filed on Nov. 13, 2008, now Pat. No. 8,263,743.

(60) Provisional application No. 60/987,651, filed on Nov. 13, 2007.

(51) Int. Cl.
*A61K 39/395* (2006.01)
*C07K 16/28* (2006.01)

(52) U.S. Cl.
CPC .......... *C07K 16/2875* (2013.01); *C07K 2317/24* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS 7,597,886 B2 * 10/2009 Yu .................... A61K 31/713
424/130.1
2002/0111325 A1   8/2002 Li et al.

FOREIGN PATENT DOCUMENTS

| WO | WO 03/039491 A2 | 5/2003 |
|----|----|----|
| WO | WO 2005/018571 A2 | 3/2005 |
| WO | WO 2006/127900 A2 | 11/2006 |
| WO | WO 2007/027751 A2 | 3/2007 |
| WO | WO 2008/106451 A2 | 9/2008 |

OTHER PUBLICATIONS

Rudikoff et al. (Proc Natl Acad Sci USA 1982 vol. 79 p. 1979.*
MacCallum et al. J. Mol. Biol. (1996) 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
International Search Report for related PCT/US2008/083362 completed Mar. 12, 2009.
Written Opinion for related PCT/US2008/083362 completed Mar. 12, 2009.
Bamias et al., Expression, Localization, and Functional Activity of TL1A, a Novel Th1-Polarizing Cytokine in Inflammatory Bowel Disease, *J. Immunol.*, 171, pp. 4868-4874 (2003).
Yu et al., "Modulation of Endothelial Cell Growth Arrest and Apoptosis by Vascular Endothelial Growth Inhibitor," *Circulation Res.*, vol. 89, pp. 1161-1167 (2001).
Bamias et al., "Role of TL1A and its Receptor DR3 in Two Models of Chronic Murine Eleitis," *Proc. Natl. Acad. Sci. USA*, 103, pp. 8441-8446 (2006).
Bossen et al., "Interactions of Tumor Necrosis Factor (TNF) and TNF Receptor Family Members in the Mouse and Human," J. Biol. Chem., 281, (20), pp. 13964-13971 (2006).
Hsu et al., "Enhanced Adhesion of Monocytes via Reverse Signaling Triggered by Decoy Receptor 3," *Exp. Cell Res.*, 292, pp. 241-251 (2004).
Wen et al., "TL1A-induced NF-kB Activation and c-IAP2 Production Prevent DR3-Mediated Apoptosis in TF-1 Cells," *J. Biol. Chem.*, 278:39251-8 (2003).
Kang et al., "Involvement of TL1A and DR3 in Induction of Pro-Inflammatory Cytokines and Matrix Metalloproteinase-9 in Atherogenesis," *Cytokine*, 29, pp. 229-235 (2005).
Kim et al., "Identification of naturally secreted soluble form of TL1A, a TNF-like cytokine," *J Immunol Methods*, 298, pp. 1-8 (2005).
Papadakis et al., Dominant Role for TL1A/DR3 Pathway in IL-12 Plus IL-18-Induced IFN-ɣ Production by Peripheral Blood and Mucosal CCR9+ T Lymphocytes[1], *The Jour.I of Immunology*, 174, pp. 4985-4990 (2005).
Migone et al., "TL1A is a TNF-like Ligand for DR3 and TR6/DcR3 and Functions as a T Cell Costimulator," Immunity., 16, pp. 479-492 (2002).
Papadakis et al., "TL1A Synergizes with IL-12 and IL-18 to Enhance IFN-ɣ Production in Human T Cells and NK Cells[1]," *J. Immunol.*, 172:7002-7007 (2004).
Prehn et al., "Potential role for TL1A, the new TNF-family member and potent costimulator of IFN-ɣ, in mucosal inflammation," *Clin. Immunol.*, 112, pp. 66-77 (2004).
Young, et al., "TL1A: A Mediator of Gut Inflammation" *Proc Natl Acad Sci U.S.A.*, 103(22), pp. 8303-8304 (2006).
Roguska et al., "A Comparison of Two Murine Monoclonal Antibodies Humanized by CDR-Grafting and Variable Domain Resurfacing," *Protein Engineering*, 9(10), pp. 895-904 (1996).

(Continued)

*Primary Examiner* — Laura B Goddard
*Assistant Examiner* — Meera Natarajan
(74) *Attorney, Agent, or Firm* — Foley & Lardner LLP

(57) ABSTRACT

Disclosed are humanized antibodies that bind specifically to TNF superfamily member 15 (TNFSF15), also known as TL1A. Methods of making and using the anti-TL1A antibodies are also described. The humanized antibodies may be antagonists and may used to treat or diagnose conditions associated with TL1A function.

22 Claims, 15 Drawing Sheets

(56) References Cited

OTHER PUBLICATIONS

Jones et al., "Replacing the Complementarity-Determining Regions in a Human Antibody with Those from a Mouse," *Nature*, vol. 321 pp. 522-525 (1986).
Studnicka et al., "Human-Engineered Monoclonal Antibodies Retain Full Specific Binding Activity by Preserving non-CDR Complementarity-Modulating Residues," *Protein Engineering*, vol. 7, No. 6, pp. 805-814 (1994).
Su et al., "Differential Regulation of Interleukin-8 Gene Transcription by Death Receptor 3 (DR3) and Type I TNF Receptor (TNFRI)," *Exper. Cell Research* 312, pp. 266-277 (2006).
Fang et al., "Essential Role of TNF Receptor Superfamily 25 (TNFRSF25) in the Development of Allergic Lung Inflammation," *J. Exp. Med.*, vol. 205, No. 5, pp. 1037-1048 (2008).
EP Communication cited in related European Patent Application No. 08850583.9, dated Feb. 9, 2012.
Rudikoff et al., "Single-Amino Acid Substitution Altering Antigen-Binding Specificity," *Proc. Natl. Acad. Sci*, vol. 79, pp. 1979-1983 (1982).
MacCallum et al., "Antibody-antigen Interactions: Contact Analysis and Binding Site Topography," *J. Mol. Biol.* vol. 262, pp. 732-745 (1996).
Pascalis et al., "Grafting of "Abbreviated" Complementarity-Determining Regions Containing Specificity-Determining Residues Essential for Ligand Contact to Engineer a Less Immunogenic Humanized Monoclonal Antibody," *The Journ. of Immun.*, vol. 169, pp. 3076-3084 (2002).
Casset et al., "A Peptide Mimetic of an Anti-CD4 Monoclonal Antibody by Rational Design," *Biochemical and biophysical Res. Communications*, vol. 307, pp. 198-205 (2003).
Vajdos et al., "Comprehensive Functional Maps of the Antigen-binding Site of an Anti-ErbB2 Antibody Obtained with Shotgun Scanning Mutagenesis," *J. Mol. Biol.*, vol. 320, pp. 415-428 (2002).
Wu et al., "Humanization of a Murine Monoclonal Antibody by Simultaneous Optimization Framework and CDR Residues," *J. Mol. Biol.*, vol. 294, pp. 151-162 (1999).

Padlan et al., "Structure of an Antibody-Antigen Complex: Crystal Structure of the HyHEL-10 Fab-Lysozyme Complex," *Proc. Natl. Acad. Sci.*, vol. 86, pp. 5938-5942 (1989).
Lamminmaki et al., "Crystal Structure of a Recombinant Anti-estradiol Fab Fragment in Complex with 17β-Estradiol," *The Journ. of Biological Chem.*, vol. 276.
Chen et al., "Selection and Analysis of an Optimized Anti-VEGF Antibody: Crystal Structure Affinity-matured Fab in Complex with Antigen," *J. Mol. Biol.*, vol. 293, pp. 865-881 (1999).
European Search Report issued in related European Patent Application No. 12172164, dated Sep. 20, 2012.
Written Opinion issued in related Singapore Application No. 201003202-7, dated May 10, 2012.
Adams et al., "Prolonged In Vivo Tumour Retention of a Human Diabody Targeting the Extracellular Domain of Human Her2/NEU," *Brit. Journ. of Cancer*, vol. 77, No. 9, pp. 1405-1412 (1998).
Le Gall et al., "Di-, tri- and Tetrameric Single Chain Fv Antibody Fragments Against Human CD19: Effect of Valency of Cell Binding," *FEBS Letters*, vol. 453, No. 1-2, pp. 164-168 (1999).
Almagro et al., "Humanization of Antibodies," *Frontiers in Bioscience*, vol. 13, pp. 1619-1633 (2008).
European Communication issued in related European Patent Application No. 12 172 164.1, dated Jul. 30, 2013.
White et al., "Antibody-Targed Immunotherapy for Treatment of Malignancy," *Ann. Rev. Med.*, vol. 52, pp. 125-145 (2001).
Rudikoff et al., "Single Amino Acid Substitution Altering Antigen-Binding Specificity," Proc. Natl. Acad. Sci USA, vol. 79, p. 1979 (1982).
Wu, "Simultaneous Humanization and Affinity Optimization of Monoclonal Antibodies," Methods in Molecular Biology, vol. 207, pp. 197-212 (2003).
Casadevall et al., "Immunoglobulin Isotype Influences Affinity and Specificity," *Proceedings of the National Academy of Sciences*, vol. 109, No. 31, pp. 12272-12273 (2012).
Summons to Attend Oral Proceedings dated Feb. 24, 2015.

\* cited by examiner

FIGURE 3

| Construct | # of Mutations | % Humanization |
|---|---|---|
| Hum VH #1 | 18 | 100 |
| Hum VH #2 | 13 | 95 |

FIGURE 5

| Construct | # of Mutations | % Humanization |
|---|---|---|
| Hum VK #1 | 8 | 87 |
| Hum VK #2 | 5 | 87 |

FIGURE 6

| Construct Names | Batch#/CID's | Protein / Conc. |
|---|---|---|
| Hum 16H02 Anti-TL1A VH#1+VK#1 | LDC 3009 | 1.1 mgs (0.4 mg/ml) |
| Hum 16H02 Anti-TL1A VH#2+VK#1 | LDC 3010 | 0.76 mgs (0.4 mg/ml) |
| Hum 16H02 Anti-TL1A VH#1+VK#2 | LDC 3011 | 2.9 mgs (1.0 mg/ml) |
| Hum 16H02 Anti-TL1A VH#2+VK#2 | LDC 3012 | 2.3 mgs (0.8 mg/ml) |

FIGURE 9

| 16H02 VK | Transfection ID | LDC # |
|---|---|---|
| WWW Ver#2 | W1 | 3030 |
| New WWW | W2 | 3031 |
| WWM | M1 | 3032 |
| MWM | M2 | 3033 |
| WMW-1 (QL) | M3 | 3034 |
| WMW-2 (RL) | M4 | 3035 |
| MWW | M5 | 3036 |
| MMW | M6 | 3037 |
| MMM | M7 | 3038 |

```
       1                    10                  20                  30
   1   Q V T L K E S G P A L V K P T Q T L T L T C T F S G F S L S    1B4    VH  AA
   1   Q V T L K E S G P A L V K P T Q T L T L T C T F S G F S L S    hum    1B4 VH AA
   1   Q V T L R E S G P A L V K P T Q T L T L T C T F S G F S L S    VH2-70-10

40                  50                  60
  31   T S N M G V S W I R Q P S G K G L E W L A H I W W D D D K R    1B4    VH  AA
  31   T S N M G V S W I R Q P P G K A L E W L A H I W W D D D K R    hum    1B4 VH AA
  31   S G M R V S W I R Q P P G K A L E W L A R I D W D D D K Y      VH2-70-10

70                  80                  90
  61   F K T S L K T R L T I S K D T S K N Q V V L T M T N M D P T    1B4    VH  AA
  61   L K T S L K T R L T I S K D T S K N Q V V L T M T N M D P V    hum    1B4 VH AA
  61   Y S T S L K T R L T I S K D T S K N Q V V L T M T N M D P V    VH2-70-10

100                 110                 120
  91   D T A T Y Y C A R M S R N Y Y G S S Y V M D Y W G Q G T S V    1B4    VH  AA
  91   D T A T Y Y C A R M S R N Y Y G S S Y V M D Y W G Q G T L V    hum    1B4 VH AA
  91   D T A T Y Y C A R                                              VH2-70-10

121   T V S S    1B4    VH  AA
 121   T V S S    hum    1B4 VH AA
  99            VH2-70-10
```

FIGURE 14

```
            1        10              20              30
1   QIQLTQSPAIMSASHGETITCSASSSVN          1B4      VK AA
1   DIQLTQSPSFLSASVGDRVTITCSASSSVS        hum 1B4  VK AA
1   DIQLTQSPSFLSASVGDRVTITCRASQGIS        VK L8

31       40              50              60
31  YNHWYQQRSGTSPKLLIYSTSNLASGVPS         1B4      VK AA
31  YNHWYQQKPGKAPKLLIYSTSNLASGVPS         hum 1B4  VK AA
31  SYLAWYQQKPGKAPKLLIYAASTLQSGVPS        VK L8

60       70              80              90
60  RFSGSGSGTDYTLTISSMEDAATYYCHQ          1B4      VK AA
60  RFSGSGSGTEFTLTISSLQPEDFATYYCHQ        hum 1B4  VK AA
61  RFSGSGSGTEFTLTISSLQPEDFATYYCQQ        VK L8

90       100
90  HNTYTFGGGTKLEIKR                      1B4      VK AA
90  HNYGTFGQGTKVEIKR                      hum 1B4  VK AA
91  LNSYPT                                VK L8
```

HUMANIZED ANTIBODIES AGAINST TL1A

CROSS-REFERENCE TO RELATED APPLICATIONS

This application is a Divisional of U.S. patent application Ser. No. 13/585,792, filed Aug. 14, 2012, which is a Divisional of U.S. patent application Ser. No. 12/270,673, filed Nov. 13, 2008, now U.S. Pat. No. 8,263,743, which claims the benefit of priority from U.S. Provisional Patent Application No. 60/987,651, filed on Nov. 13, 2007. The contents of these applications are hereby incorporated by reference in their entirety.

SEQUENCE LISTING

The instant application contains a Sequence Listing which has been submitted electronically in ASCII format via EFS-web and is hereby incorporated by reference in its entirety. Said ASCII copy, created on Jul. 7, 2014, is named 075977-0279 SL.txt and is 72,106 bytes in size.

SUMMARY

The present invention is directed to antibodies against TL1A, and methods of making and using such antibodies. The antibodies are expected to be particularly useful in treating inflammatory conditions such as Crohn's disease.

BACKGROUND

Proteins that are structurally related to tumor necrosis factor (TNF) are collectively referred to as the TNF superfamily. TL1A, a TNF superfamily member, is a TNF-like cytokine that binds to the death-domain receptor (DR)3 and provides costimulatory signals to activated lymphocytes. Through this interaction, TL1A induces secretion of IFN-gamma and may, therefore, participate in the development of T helper-1-type effector responses.

TL1A is a type II transmembrane protein and has been designated TNF superfamily member 15 (TNFSF15). TL1A is expressed predominantly by endothelial cells and monocytes, and its expression is inducible by TNF-a and IL-1a. Migone et al., *Immunity*, 16:479-92 (2002). TL1a is upregulated by the proinflammatory cytokines TNF and IL-1 and also by immune complexes (IC). Hsu et al., *Exp. Cell Res.*, 292:241-51 (2004).

TL1A mediates signaling via its cognate receptor DR3, a death receptor whose activation was known to induce both death and survival factors. TL1A, like TNF, is also presumed to circulate as a homotrimeric soluble form. Kim et al., *J. Immunol. Methods*, 298(1-2):1-8 (March 2005).

TL1A binds with high affinity to death receptor 3 (DR3) which is a member of the death-domain containing TNF receptor family, and is also termed Wsl-1, Apo-3, TRAMP, and LARD, and now designated TNF receptor superfamily member 25 (TNFRSF25). Depending on the cell context, ligation of DR3 by TL can trigger one of two signaling pathways, activation of the transcription factor NF-kB or activation of caspases and apoptosis. TL1 functions in T cell costimulation and Th1 polarization. On activated T cells, TL1A functions specifically via its surface-bound receptor DR3 to promote cell survival and secretion of proinflammatory cytokines. The secreted decoy receptor 3 (DcR3), a soluble protein of the tumor necrosis factor receptor (TNFR) superfamily, blocks the action of TL1A. Kim et al., "Identification of naturally secreted soluble form of TL1A, a TNF-like cytokine," *J Immunol Methods*, 298:1-8 (2005).

Potential Therapeutic Targets

Allergy and Asthma

Th2 polarization of CD4 T cells with elevated IgE levels and production of IL-13 by NKT cells are major cause of lung inflammation in Allergy and asthma. TL1A plays a major role in allergic lung inflammation (Fang et al J. Exp. Med. 2008). TL co-stimulates IL-4 and IL-13 production in NKT cells. Blocking TL1A and DR3 interaction by TL1A antibody or dominant negative TL1A mutant abolishes lung inflammation.

Lung and Colon Carcinomas

Members in the TNF and its receptor superfamilies regulate immune responses and induce apoptosis. DR3 is preferentially expressed by T lymphocytes and upregulated during T cell activation. The ligand for DR3 is TL1A. TL1A also binds decoy receptor DcR3/TR6, which is expressed in several lung and colon carcinomas and in some normal tissues. TL1A is upregulated by proinflammatory cytokines TNF and IL-1. TL1A is a longer variant of TL1 (also called VEGI).

Atherosclerosis

In addition, TL1A has also been reported to be angiostatic and to induce metalloproteinase and IL-8 gene expression (Su et al., *Exp. Cell Res.*, 312:266-277 (2006); Kang et al., *Cytokine*, 29:229-235 (2005)). Indeed, TL1A and DR3 may be involved in the pathogenesis of atherosclerosis by increasing the production of proinflammatory cytokines and chemokines and decreasing plaque stability by inducing extracellular matrix-degrading enzymes (Kang et al., *Cytokine*, 29:229-235 (2005)).

Rheumatoid Arthritis

There is also evidence to suggest that TL1A/DR3 is involved in the etiology of rheumatoid arthritis (Bossen et al., J. Biol. Chem., 281(20):13964-13971 (May 19, 2006).

Inflammatory Bowel Disease

Researchers have found an association of the expression of TL1A and inflammatory bowel disease (Prehn et al., *Clin. Immunol.*, 112:66-77 (2004); Bamias et al., *J. Immunol.*, 171: 4868-4874 (2003)).

Th1-Mediated Intestinal Diseases, Such as Crohn's Disease

Crohn's disease is a severe inflammatory bowel disorder that strikes young adults (ages 20-30). The condition is thought to originate from predisposing genetic and environmental factors that cause an imbalance of effector (proinflammatory) and regulatory T cell responses, resulting in inflammation of the gastrointestinal mucosa and disease.

The TL1A/DR3 pathway plays an important role in Th1-mediated intestinal diseases, such as Crohn's disease. Konstantinos et al., *The Journal of Immunology*, 2005, 174: 4985-4990 (2005); Bamias et al., *J. Immunol.*, 171:4868-74 (2003). Blockade of the TL1A/DR3 pathway may, therefore, offer therapeutic opportunities in Crohn's disease.

TL1A augments IFN-gamma production by anti-CD3 plus anti-CD28 and IL-12/IL-18-stimulated peripheral blood (PB) T cells. Activation of DR3 by TL induced the formation of a signaling complex containing TRADD, TRAF2, and RIP and activated the NF-kB and the ERK, JNK, and p38 mitogen-activated protein kinase pathways. Kang et al., *Cytokine*, 29:229-35 (2005). TL1A can be released to circulate as a homotrimeric soluble form. Wen et al., "TL1A-induced NF-kappaB activation and c-IAP2 production prevent DR3-mediated apoptosis in TF-1 cells," *J. Biol. Chem.*, 278:39251-8 (2003).

Death receptors and their ligands play a key role in the maintenance of tissue homeostasis and the physiological regulation of programmed cell death. Binding of a death ligand induces oligomerization of the receptor, recruitment of an adapter protein via a conserved cytoplasmic signaling element termed the death domain, activation of caspases, and induction of apoptosis. Young et al., *Proc Natl. Acad. Sci. USA.*, 103(22): 8303-8304 (May 30, 2006).

Although death receptors such as Fas/Apo-1/CD95, TNF-R1, TRAIL-R1, TRAIL-R2, or DR3 were initially characterized as inducers of apoptosis, there is growing evidence that these receptors also have nonapoptotic functions, including regulation of the adaptive immune response. Bamias et al., *Proc. Natl. Acad. Sci. USA,* 103:8441-8446 (2006), report that TL1A is expressed by lamina propia dendritic cells and that it functions by increasing the proliferation of memory cells, but not naïve $CD4^+$ T cells, and synergizes with IL-12 and/or low-dose stimulation of the T cell receptor to strongly enhance IFN-γ gene expression. IFN-γ expression in the gut has been considered a marker of inflammation, and many strategies for treating Crohn's disease rely on broad attempts to suppress the immune-activated state. However, such approaches (steroid treatment and immunosuppressive drugs) do not focus on the gut specifically and thus have their own complications. Targeted therapies based on the use of antagonists of TNF-α were introduced with success in the 1990s, and the results reported in ref. 1 suggest that therapy directed specifically against TL1A or its receptor may provide an alternative targeted therapy for this debilitating disorder.

As reported in Bamias et al., *Proc. Natl. Acad. Sci. USA.,* 103:8441-8446 (2006), TL1A seems to have a most profound effect when expressed in the gut during inflammation. TL1A synergizes in the induction of IFN-γ expression in human T cells when combined with IL-12/18, although increased expression can also be observed in natural killer cells (Migone et al., *Immunity.*, 16:479-492 (2002); Papadakis et al., *J. Immunol.*, 174:4985-4990 (2005); Papadakis et al., *J. Immunol.,* 172:7002-7007 (2004)). Bamias et al., *Proc. Natl. Acad. Sci. USA.,* 103:8441-8446 (2006), is the first report of a similar observation in mouse models of Crohn's disease and extends earlier data by showing that the synergy occurs when the T cell receptor is weakly stimulated or T cells are treated with IL-12. Although in Bamias et al. no synergy is observed when TL1A treatment is combined with IL-18 this result may not be surprising because both IL-18 and TL1A signal through NF-κB. Whereas the initial report by Migone et al. on TL1A demonstrated that it was a T cell costimulatory signal, Bamias et al. demonstrate that it is the memory T cell that most strongly responds, consistent with the increased capacity of this T cell population to express IFN-γ. Because this population does proliferate, it also expresses higher levels of the TL1A receptor, thus further enhancing the ability of the cells to proliferate and express IFN-γ. This finding might be considered somewhat surprising given that the only known receptor of TL1A is DR3, a death domain-containing receptor, and it might have been hypothesized that triggering this receptor would lead to cell death. (TL1A signals through DR3, its only known cell surface receptor. TL1A also binds to the soluble decoy receptor (DcR3)). However NF-κB-dependent antiapoptotic genes, such as inhibitor of apoptosis 2, have been shown to be induced by TL1A (Wen et al., *J. Biol. Chem.,* 278:39251-39258 (2003)), and therefore triggering of apoptosis vs. proliferation may be cell-type dependent.

Current treatment options for Crohn's disease include the monoclonal antibody against TNF-α infliximab (Remicade; Centocor, Inc., Horsham, Pa.), the monoclonal antibody Adalimumab (brand name Humira; Abbott), as well as anti-inflammatories (e.g., sulfasalazine), cortisone or steroids (e.g., prednisone), immune system suppressors (e.g. 6-mercaptopurine), and antibiotics. However, infliximab is the only treatment option having a high degree of specificity; the remaining treatment options have a low specificity. *Proc Natl Acad Sci U.S.A.,* 103(22): 8303-8304 (May 30, 2006). This means that the treatment is not targeted to the disease area. While infliximab has a high specificity and is generally well tolerated, infliximab can cause recrudescence of tuberculosis infection and worsening of heart failure, demyelinating disease, and an increased incidence of lymphoma.

Therefore, there remains a need in the art for compositions that can be used in the treatment and diagnosis of diverse inflammatory and immune diseases and disorders, such as allergy/asthma, rheumatoid arthritis, multiple sclerosis, Crohn's disease, inflammatory bowel disease, chronic obstructive pulmonary disease, psoriasis, type 1 diabetes and transplant rejection. The present invention, directed to monoclonal antibodies against TL1A, satisfies this need.

SUMMARY

Disclosed are antigen-binding polypeptide molecules that bind specifically to the TNF-like cytokine TL1A (see GenBank accession no. AF520785). The polypeptides include a humanized heavy chain variable region and a humanized light chain variable region. For example, the polypeptides may include the framework (FR) regions of the light and heavy chain variable regions of a human antibody, while retaining substantially the antigen-binding specificity of a parental monoclonal antibody. The humanized heavy chain variable region and/or the humanized light chain variable region are at least about 87% humanized, at least about 90% humanized, at least about 95% humanized, at least about 98% humanized, or at least about 100% humanized, excluding the complementary-determining regions (CDRs). The antigen-binding polypeptides molecules may be derived from monoclonal antibody donors (e.g., mouse monoclonal antibody donors) and may include CDRs from the monoclonal antibodies (e.g., mouse monoclonal CDRs). The polypeptides may function as antagonists for the TL1A receptor.

Also encompassed by the invention are pharmaceutical compositions comprising the polypeptides of the invention, methods of making such polypeptides and compositions, and methods of treating subjects in need with the compositions of the invention. Exemplary conditions that may be treated with the compositions of the invention include, but are not limited to autoimmune disease (e.g., lupus), inflammatory bowel disease (IBD), chronic obstructive pulmonary disease (COPD), arthritis (e.g., rheumatoid arthritis), multiple sclerosis, transplant rejection, central nervous system injury, Th1-mediated intestinal diseases such as Crohn's disease, psoriasis, leukemia or lymphoma (e.g., chronic lymphocytic leukemia (CLL)), atherosclerosis, and lung and colon carcinomas.

In some embodiments, the antigen-binding polypeptide binds specifically to TL1A, and includes: (a) a humanized antibody heavy chain variable region comprising: (1) a CDR-H1 comprising an amino acid sequence of ({L,S,N}Y{G,A}MN) (SEQ ID NO: 1); (2) a CDR-H2 comprising an amino acid sequence of (WINT{Y,N}TG{E,N}PTYA{D,Q}{D,G}F{K,T}G) (SEQ ID NO: 2); and (3) a CDR-H3 comprising an amino acid sequence of (D{T,Y}{A,G}{M,K}{D,Y}{Y,G}{A,D}{M,Y}{A,Y}{Y,A}MDY) (SEQ ID NO: 3); and (b) a humanized antibody light chain variable region comprising: (1) a CDR-L1 comprising an amino acid sequence of ({K,R}SSQ{N,S}{I,L}V{H,Y}S{D,N}GNTYL{E,N,D}) (SEQ ID NO: 4); (2) a CDR-L2 comprising an amino acid sequence of (KVSNR{F,D}S) (SEQ ID NO: 5); and (3) a CDR-L3 comprising an amino acid sequence of ({F, M}QG{S,T}H{V,-}{P,-}{T,-}) (SEQ ID NO: 6).

In certain embodiments the antigen-binding polypeptide binds specifically to TL1A and includes: a humanized antibody heavy chain variable region comprising (1) the CDR-H1 comprising, consisting essentially of or consisting of the amino acid sequence of TSNMGVV (SEQ ID NO: 7); (2) the CDR-H2 comprising, consisting essentially of or consisting of the amino acid sequence of HILWDDREYSNPALKS (SEQ ID NO: 8); and (3) the CDR-H3 comprising, consisting essentially of or consisting of the amino acid sequence of MSRNYYGSSYVMDY (SEQ ID NO: 9).

In some embodiments, the antigen-binding polypeptide comprises a humanized antibody heavy chain variable region comprising, consisting essentially of or consisting of the amino acid sequence of:

```
                                             (SEQ ID NO: 10)
QVTLKESGPALVKPTQTLTLTCTFSGESLSTSNMGVVWIRQPPGKA

LEWLAHILWDDREYSNPALKSRLTISKDTSKNQVVLTMTNMDPVDT

ATYYCARMSRNYYGSSYVMDYWGQGTLVTVSS.
```

In some embodiments of the polypeptides, (1) the CDR-H1 consists of the amino acid sequence of (LYGMN) (SEQ ID NO: 11) or (NYGMN) (SEQ ID NO: 12); (2) the CDR-H2 consists of the amino acid sequence of (WINTYTGEPTYADDFKG) (SEQ ID NO: 13); (3) the CDR-H3 consists of the amino acid sequence of (DTAMDYAMAY) (SEQ ID NO: 14) or DYGKYGDYYAMDY (SEQ ID NO: 15); (4) the CDR-L1 consists of the amino acid sequence of (KSSQNIVHSDGNTYLE) (SEQ ID NO: 16) or (RSSQSIVHSNGNTYLD) (SEQ ID NO: 17); (5) the CDR-L2 consists of the amino acid sequence of (KVSNRFS) SEQ ID NO: 18); and (6) the CDR-L3 consists of the amino acid sequence of (FQGSHVPLT) (SEQ ID NO: 19).

In some embodiments, the polypeptide comprises a humanized antibody heavy chain variable region of

```
                                             (SEQ ID NO: 20)
(Q{V,I}QLVQSG{S,P}ELKKPG{A,E}{S,T}VK{V,I}SCKAS

GYTFT{L,S,N}Y{G,A}MNWV{R,K}QAPG{Q,K}GL{E,K}WMG

WINT{Y,N}TG{E,N}PTYA{D,Q}{D,G}F{K,T}GRF{V,A}FS

L{D,E}TS{V,A}STAYLQI{S,N}{S,T}LK{A,N}ED{T,M}A

{V,T}Y{Y,F}CARD{T,Y}{A,G}{M,K}{D,Y}{Y,G}{A,D}

{M,Y}{A,Y}{Y,A}MDY)WGQGT{L,S}VTVSS).
```

For example, the polypeptide may comprise a humanized antibody heavy chain variable region of

```
                                             (SEQ ID NO: 21)
(QVQLVQSGSELKKPGASVKVSCKASGYTFTLYGMNWVRQAPGQGL

EWMGWINTYTGEPTYADDFKGRFVFSLDTSVSTAYLQISSLKAEDT

AVYYCARDTAMDYAMAYWGQGTLVTVSS)
or
                                             (SEQ ID NO: 22)
(QVQLVQSGSELKKPGASVKVSCKASGYTFTLYGMNWVKQAPGKGL

KWMGWINTYTGEPTYADDFKGRFVFSLDTSVSTAYLQISSLKAEDT

AVYFCARDTAMDYAMAYWGQGTLVTVSS).
```

Alternatively, the polypeptide may comprise a humanized antibody heavy chain variable region of

```
                                             (SEQ ID NO: 23)
(QVQLVQSGSELKKPGASVKVSCKASGYTFTNYGMNWVRQAPGQGL

EWMGWINTYTGEPTYADDFKGRFVFSLDTSVSTAYLQISSLKAEDT

AVYYCARDYGKYGDYYAMDYWGQGTLVTVSS)
or
                                             (SEQ ID NO: 24)
(QVQLVQSGSELKKPGASVKVSCKASGYTFTNYGMNWVRQAPGKGL

KWMGWINTYTGEPTYADDFKGRFVFSLDTSVSTAYLQISSLKAEDT

AVYFCARDYGKYGDYYAMDYWGQGTLVTVSS).
```

In some embodiments, the polypeptide comprises a humanized antibody light chain variable region of

```
                                             (SEQ ID NO: 25)
(DVVMTQ{T,S}PLSLPV{T,S}{P,L}G{E,D,Q}{P,Q}ASISC

{K,R}SSQ{N,S}{I,L}V{H,Y}SDGNTYL{E,N}W{Y,F}{L,Q}

Q{K,R}PGQSP{Q,K,R}{L,V,R}LIY KVSNR{F,D}SGVPDRFS

GSGSGTDFTLKI{S,N}RVEAED{L,V}GVY{Y,F}C{F,M}QG{S,

T}H{V,-}{P,-}{L,-}{T,-}{F,W}G{G,S,Q}GTK{V,L}EI

KR).
```

For example, the polypeptide may comprise a humanized antibody light chain variable region of

```
                                             (SEQ ID NO: 26)
(DVVMTQTPLSLPVTPGEPASISCKSSQNIVHSDGNTYLEWYLQKP

GQSPQLLIYKVSNRFSGVPDRFSGSGSGTDFTLKISRVEAEDLGVYY

CFQGSHVPLTFGGGTKVEIKR)
or
                                             (SEQ ID NO: 27)
(DVVMTQSPLSLPVTLGQPASISCKSSQNIVHSDGNTYLEWFQQRPG

QSPRRLIYKVSNRFSGVPDRFSGSGSGTDFTLKISRVEAEDVGVYYC

FQGSHVPLTFGGGTKVEIKR).
```

In another embodiment, the polypeptide may comprise a humanized antibody light chain variable region of

```
                                             (SEQ ID NO: 28)
(DVVMTQSPLSLPVTLGQPASISCKSSQNIVHSDGNTYLEWFQQRPG

QSPRRLIYKVSNRFSGVPDRFSGSGSGTDFTLKISRVEAEDVGVYYC

FQGSHVPLTFGQGTKVEIKR).
```

Also disclosed are humanized antibody heavy chain variable regions. The humanized antibody heavy chain region may comprise: (1) a CDR-H1 comprising an amino acid sequence of ({L,S,N}Y{G,A}MN) (SEQ ID NO: 29); (2) a CDR-H2 comprising an amino acid sequence of (WINT{Y,N}TG{E,N}PTYA{D,Q}{D,G}F{K,T}G) (SEQ ID NO: 2); and (3) a CDR-H3 comprising an amino acid sequence of (DTAMDYAMAY) (SEQ ID NO: 14). For example, the humanized antibody heavy chain variable region may comprise an amino acid sequence of

```
                                                (SEQ ID NO: 21)
(QVQLVQSGSELKKPGASVKVSCKASGYTFTLYGMNWVRQAPGQGLE

WMGWINTYTGEPTYADDFKGRFVFSLDTSVSTAYLQISSLKAEDTAV

YYCARDTAMDYAMAYWGQGTLVTVSS).
```

Alternatively, the polypeptide may comprise a humanized antibody heavy chain variable region of

```
                                                (SEQ ID NO: 22)
(QVQLVQSGSELKKPGASVKVSCKASGYTFTLYGMNWVKQAPGKGLK

WMGWINTYTGEPTYADDFKGRFVFSLDTSVSTAYLQISSLKAEDTAV

YFCARDTAMDYAMAYWGQGTLVTVSS).
```

In another example, a humanized antibody heavy chain variable region comprises: (1) a CDR-H1 comprising an amino acid sequence of (NYGMN) (SEQ ID NO: 12); (2) a CDR-H2 comprising an amino acid sequence of (WINTYT-GEPTYADDFKG) (SEQ ID NO: 13); and (3) a CDR-H3 comprising an amino acid sequence of (DYGKYGDYYAMDY) (SEQ ID NO: 15). For example, the humanized antibody heavy chain variable region may comprise an amino acid sequence of

```
                                                (SEQ ID NO: 23)
(QVQLVQSGSELKKPGASVKVSCKASGYTFTNYGMNWVRQAPGQGLE

WMGWINTYTGEPTYADDFKGRFVFSLDTSVSTAYLQISSLKAEDTAV

YYCARDYGKYGDYYAMDYWGQGTLVTVSS).
```

Alternatively, the polypeptide may comprise a humanized antibody heavy chain variable region of

```
                                                (SEQ ID NO: 30)
(QVQLVQSGSELKKPGASVKVSCKASGYTFTNYGMNWVKQAPGKGLK

WMGWINTYTGEPTYADDFKGRFVFSLDTSVSTAYLQISSLKAEDTAV

YFCARDYGKYGDYYAMDYWGQGTLVTVSS).
```

In another example, a humanized antibody heavy chain variable region comprises: (1) a CDR-H1 comprising an amino acid sequence of (NYAMS) (SEQ ID NO: 31); (2) a CDR-H2 comprising an amino acid sequence of (TIYSGGGYTFYLDSLKG) (SEQ ID NO: 32); and (3) a CDR-H3 comprising an amino acid sequence of (HSYPMT-TVITYAPYYFYY) (SEQ ID NO: 33). For example, the humanized antibody heavy chain variable region may comprise an amino acid sequence of

```
                                                (SEQ ID NO: 34)
(QVQLVQSGSELKKPGASVKVSCKASGYTFTNYAMSWVKQAPGKGLK

WMGTIYSGGGYTFYLDSLKGRFVFSLDTSVSTAYLQSSLKAEDTAVY

FCARHSYPMTTVITYAPYYFYYWGQGTLVTVSS).
```

Also disclosed are humanized antibody light chain variable regions. The humanized antibody light chain variable region may comprise: (1) a CDR-L1 comprising an amino acid sequence of ({K,R}SSQ{N,S}{I,L}V{H,Y}S{D,N}GNTYL{E,N,D}) (SEQ ID NO: 4); (2) a CDR-L2 comprising an amino acid sequence of (KVSNR{F,D}S) (SEQ ID NO: 5); and (3) a CDR-L3 comprising an amino acid sequence of ({F,M}QG{S,T}H{V,-}{P,-}{L,-}{T,-}) (SEQ ID NO: 6).

In other embodiments the antigen-binding polypeptide binds specifically to TL1A and includes: a humanized antibody light chain variable region comprising: (1) a CDR-L1 comprising, consisting essentially of, or consisting of an amino acid sequence of SASSSVNYMH (SEQ ID NO: 35); (2) a CDR-L2 comprising, consisting essentially of, or consisting of an amino acid sequence of STSNLAS (SEQ ID NO: 36); and (3) a CDR-L3 comprising, consisting essentially of, or consisting of an amino acid sequence of HQWNNYGT (SEQ ID NO: 37).

In some embodiments, the antigen-binding polypeptide comprises a humanized antibody light chain variable region comprising, consisting essentially of or consisting of the amino acid sequence of:

```
                                                (SEQ ID NO: 38)
DIQLTQSPSFLSASVGDRVTITCSASSSVNYMHWYQQKPGKAPKLL

IYSTSNLASGVPSRFSGSGSGTEFTLTISSLQPEDFATYYCHQWNN

YGTEGQGTKVEIKR.
```

For example, the humanized antibody light chain variable region may comprise an amino acid sequence of

```
                                                (SEQ ID NO: 27)
DVVMTQSPLSLPVTLGQPASISCKSSQNIVHSDGNTYLEWFQQRPGQ

SPRRLIYKVSNRFSGVPDRFSGSGSGTDFTLKISRVEAEDVGVYYCF

QGSHVPLTFGGGTKVEIKR).
```

In another embodiment, the polypeptide may comprise a humanized antibody light chain variable region of

```
                                                (SEQ ID NO: 28)
(DVVMTQSPLSLPVTLGQPASISCKSSQNIVHSDGNTYLEWFQQRPG

QSPRRLIYKVSNRFSGVPDRFSGSGSGTDFTLKISRVEAEDVGVYYC

FQGSHVPLTFGQGTKVEIKR).
```

Alternatively, the polypeptide may comprise a humanized antibody light chain variable region of

```
                                                (SEQ ID NO: 39)
DVVMTQTPLSLPVTPGEPASISCKSSQNIVHSDGNTYLEWYLQKPGQ

SPQLLIYKVSNRFSGVPDRFSGSGSGTDFTLKISRVEAEDVGVYYCF

QGSHVPLTFGGGTKVEIKR
or
                                                (SEQ ID NO: 40)
DVVMTQTPLSLPVSLGDQASISCKSSQNIVHSDGNTYLEWYLQKPGQ

SPKVLIYKVSNRFSGVPDRFSGSGSGTDFTLKINRVEAEDVGVYFCF

QGSHVPLTFGGGTKLEIKR.
```

The humanized antibody light chain region may also comprise: (1) a CDR-L1 comprising an amino acid sequence of (RSSQSIVHSNGNTYLD) (SEQ ID NO: 17); (2) a CDR-L2 comprising an amino acid sequence of (KVSNRFS) (SEQ ID NO: 18); and (3) a CDR-L3 comprising an amino acid sequence of (FQGSHVPLT) (SEQ ID NO: 19). For example, the humanized antibody light chain variable region may comprise an amino acid sequence of

```
                                             (SEQ ID NO: 41)
(DVVMTQSPLSLPVTLGQPASISCRSSQSIVHSNGNTYLDWFQQRPG

QSPRRLIYKVSNRFSGVPDRFSGSGSGTDFTLKISRVEAEDVGVYYC

FQGSHVPLTFGGGTKVEIKR.
```

Alternatively, the polypeptide may comprise a humanized antibody light chain variable region of

```
                                             (SEQ ID NO: 42)
   (DVVMTQSPLSLPVTLGQPASISCRSSQSIVHSNGNTYLDWFQQRP

GQSPRRLIYKVSNRFSGVPDRFSGSGSGTDFTLKISRVEAEDVGVY

YCFQGSHVPLTFGQGTKVEIKR)).
```

In another example, a humanized antibody light chain variable region comprises: (1) a CDR-L1 comprising an amino acid sequence of (RSSQSIVHSNGNTYLD) (SEQ ID NO: 17); (2) a CDR-L2 comprising an amino acid sequence of (KVSNRFS) (SEQ ID NO: 18); and (3) a CDR-L3 comprising an amino acid sequence of (FQGSHVPLT) (SEQ ID NO: 19). For example, the humanized antibody light chain variable region may comprise an amino acid sequence of

```
(DVVMTQTPLSLPVTPGEPASISCRSSQSIVHSNGNTYLDWYLQKP

GQSPQLLIYKVSNRFSGVPDRFSGSGSGTDFTLKISRVEAEDLGVY

YCFQGSHVPLTFGGGTKVEIKR) (SEQ ID NO: 43))
or (DVVMTQTPLSLPVSLGDQASISCRSSQSIVHSNGNTYLDWYLQKP

GQSPKVLIYKVSNRFSGVPDRFSGSGSGTDFTLKINRVEAEDLGVY

FCFQGSHVPLTFGGGTKLEIKR) (SEQ ID NO: 44)).
```

The aforementioned humanized heavy chains and humanized light chains may be present in the antigen binding polypeptides that binds specifically to TL1A.

The antigen-binding polypeptide may be selected from the group consisting of an antibody molecule, a Fab fragment, a Fab' fragment, a F(ab')$_2$ fragment, and an scFv molecule. In some embodiments, the polypeptide is an antibody molecule. Antibody molecules may include chimeric antibodies that include a human heavy chain constant region and a human light chain constant region. For example, the antibody molecule may be an IgG molecule (e.g., a IgG1 or an IgG4 molecule), where the polypeptide includes the heavy chain and light chain constant domains of an IgG molecule. The polypeptide may be an scFv molecule. For example, the scFv may have a formula selected from the group consisting of NH$_2$-L-VH-X-VK-COOH and NH$_2$-L-VK-X-VH-COOH; wherein L is a leader sequence; VH is the humanized antibody heavy chain variable region; X is a linking polypeptide; and VK is the humanized antibody light chain variable region. The polypeptide may be an Fab HSA fusion molecule. For example, the Fab HSA fusion has a formula selected from the group consisting of NH$_2$-VH-CH1-HSA-COOH combined with NH$_2$-VK-CK-COOH; wherein the VH-CH1-HSA is the humanized antibody heavy chain variable region (VH) and human constant heavy chain domain 1 (CH1) produced as a fusion protein with human serum albumin (HSA) that then folds with its cognate humanized antibody light chain variable region (VK) and human constant kappa domain (CK) to form the Fab HSA fusion protein.

The antigen-binding polypeptide further may be conjugated or fused to a therapeutic or diagnostic agent. For example, therapeutic agents may be selected from the group consisting of a cytotoxic agent, a radioactive label, an immunomodulator, a hormone, an enzyme, an oligonucleotide, a photoactive therapeutic agent or a combination thereof. Examples of diagnostic agents may include a radioactive label, a photoactive diagnostic agent, an ultrasound-enhancing agent or a non-radioactive label.

The antigen-binding polypeptide may be an antagonist of TL1A. Typically, the polypeptide is not an agonist of TL1A.

The antigen-binding polypeptide binds to the TL1A receptor with specificity and high affinity. Typically, the polypeptide binds to TL1A with an affinity constant of at least about $10^6 M^{-1}$ (preferably at least about $10^7 M^{-1}$, more preferably at least about $10^8 M^{-1}$, even more preferably at least about $10^9 M^{-1}$).

Also disclosed are pharmaceutical compositions comprising the aforementioned antigen-binding polypeptides and a carrier, such as a diluent or excipient. The pharmaceutical may further comprise an additional therapeutic or diagnostic agent as disclosed herein.

Also disclosed are methods of treating or diagnosing a disease or condition that comprise administering the disclosed pharmaceutical compositions to a patient in need thereof. For example, the pharmaceutical compositions may be administered to treat or diagnose an inflammatory, immune, and/or malignant disease or condition. Examples of diseases and conditions may include autoimmune disease (e.g., lupus), inflammatory bowel disease (IBD), chronic obstructive pulmonary disease (COPD), arthritis (e.g., rheumatoid arthritis), multiple sclerosis, transplant rejection, central nervous system injury, Crohn's disease, psoriasis, type 1 diabetes, lung and colon carcinomas, and leukemia or lymphoma (e.g., chronic lymphocytic leukemia (CLL)).

Also disclosed are polynucleotides that encode the aforementioned polypeptides. The polynucleotides may be operably linked to a promoter for expressing the encoded polypeptides in a suitable host cell. As such, methods of producing the polypeptide encoded by the recombinant polynucleotide may include: a) culturing a cell transformed with the recombinant polynucleotide to express the encoded polypeptide; and b) recovering the polypeptide so expressed.

Both the foregoing general description and the following brief description of the drawings and detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIG. 2 discloses the majority sequences as SEQ ID NO; 68.

FIG. 3 illustrates the number of mutations from mouse to human and percent humanization of two versions of a humanized anti-TL1A VH.

FIG. 4 discloses the majority sequence as SEQ ID NO: 71.

FIG. 5 illustrates the number of mutations from mouse to human and percent humanization of two versions of humanized anti-TL1A 16H02 VK.

FIG. 6 illustrates results of a transient transfection of 293F cells with human 16H02 anti-TL1A VH#1 and VH#2 and human 16H02 VK#1 and VK#2 to produce a full length humanized antibody molecule.

FIG. 8 discloses the majority sequence as SEQ ID NO: 75.

FIG. 9 illustrates the transient transfection ID and LDC # for final versions of the humanized 16H02 VK. Synthetic light chains were generated that contained all possible combinations of either wild type (W) or mutant (M) sequence in 3 distinct regions or blocks of New Hum 16H02 VK#2 from FIG. 8. The synthetic light chains were then cotransfected with New Hum 16H02 VH#1 from FIG. 2 and the resulting antibodies tested for inhibition of huTL1A-induced Caspase activity.

Figure 11:
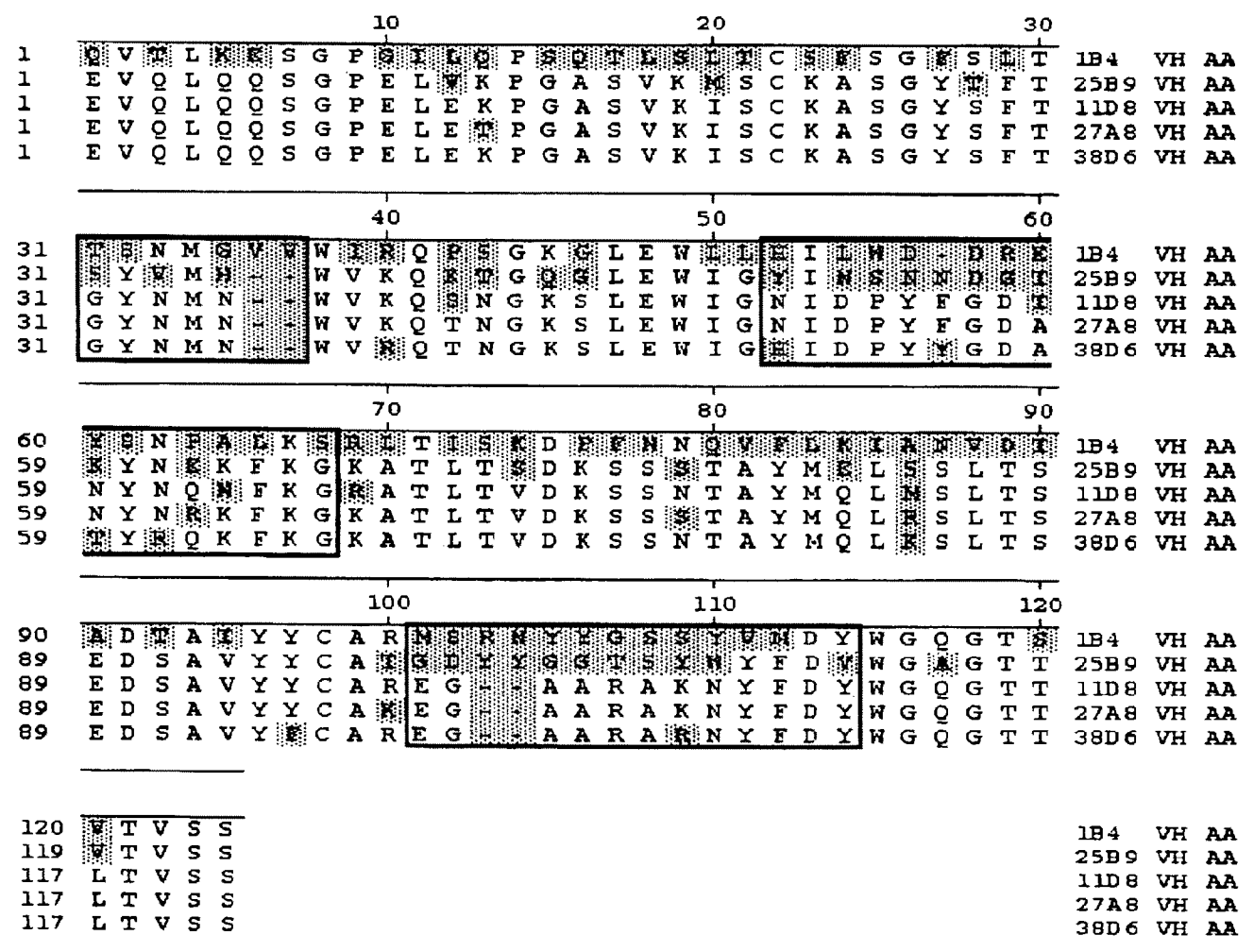

FIG. 11 illustrates a sequence alignment of the VH Domain of five lead candidate mouse anti-TL1A antibodies: 1B4 (SEQ ID NO: 58), 25B9 (SEQ ID NO: 59), 11D8 (SEQ ID NO: 60), 27A8 (SEQ ID NO: 61), and 38D6 (SEQ ID NO: 62).

Figure 12:
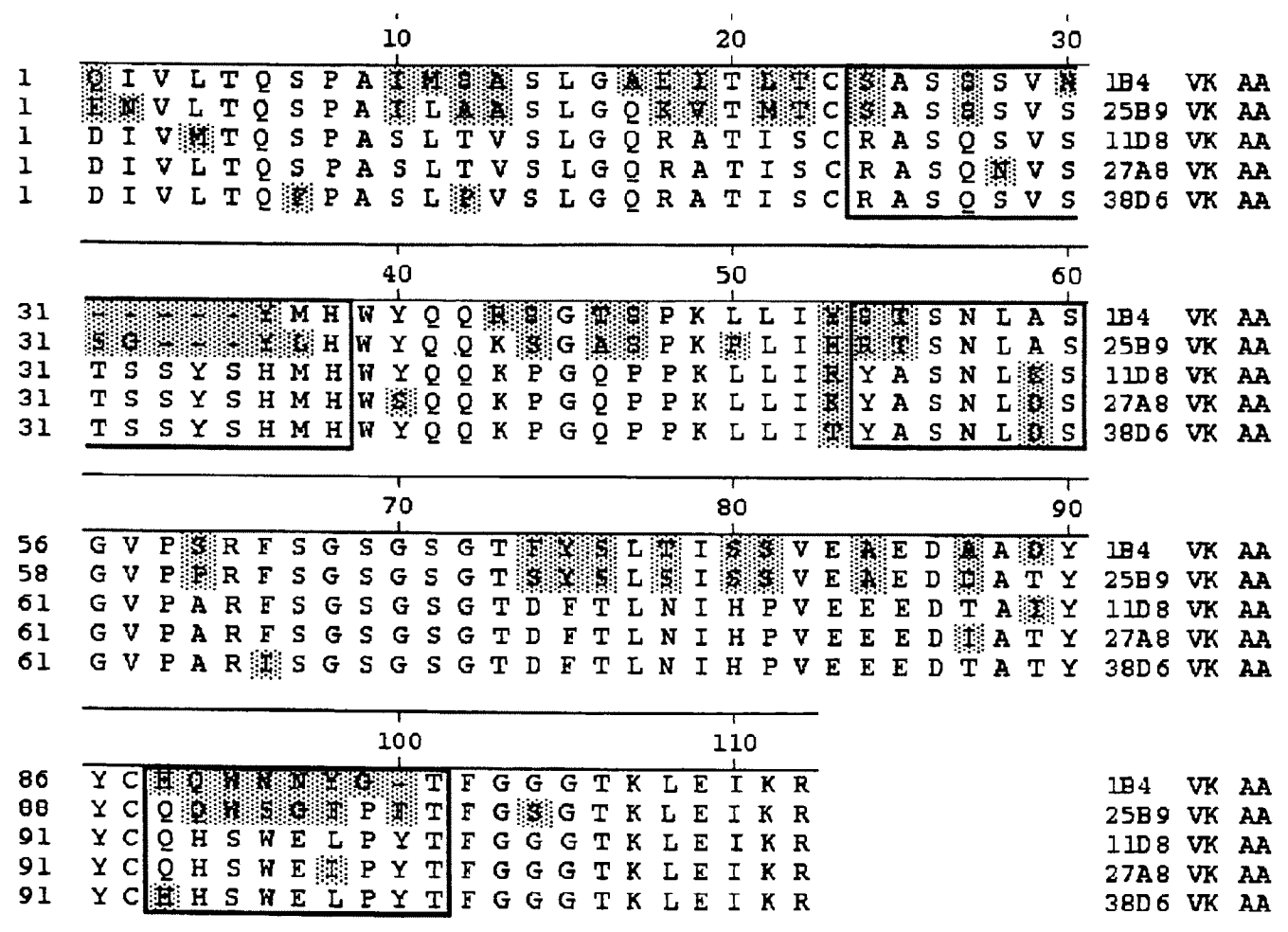

FIG. 12 illustrates a sequence alignment of the VK Domain of five lead candidate mouse anti-TL1A antibodies: 1B4 (SEQ ID NO: 49), 25B9 (SEQ ID NO: 50), 11D8 (SEQ ID NO: 52), 27A8 (SEQ ID NO: 51), and 38D6 (SEQ ID NO: 53).

FIG. 13 illustrates a sequence alignment of the humanized 1B4 VH domain (hum 1B4 VH AA) (SEQ ID NO: 77) with the original mouse VH domain (1B4 VH AA) (SEQ ID NO: 58) and the closest matching human germline VH domain (VH2-70-10) (SEQ ID NO: 79.

FIG. 14 illustrates a sequence alignment of the humanized 1B4 VK domain (hum 1B4 VK AA) (SEQ ID NO: 67) with the original mouse VK domain (1B4 VK AA) (SEQ ID NO: 49) and the closest matching human germline VK domain (VK-L8) (SEQ ID NO: 78).

DETAILED DESCRIPTION OF THE PREFERRED EMBODIMENTS

Definitions

Figure 1:
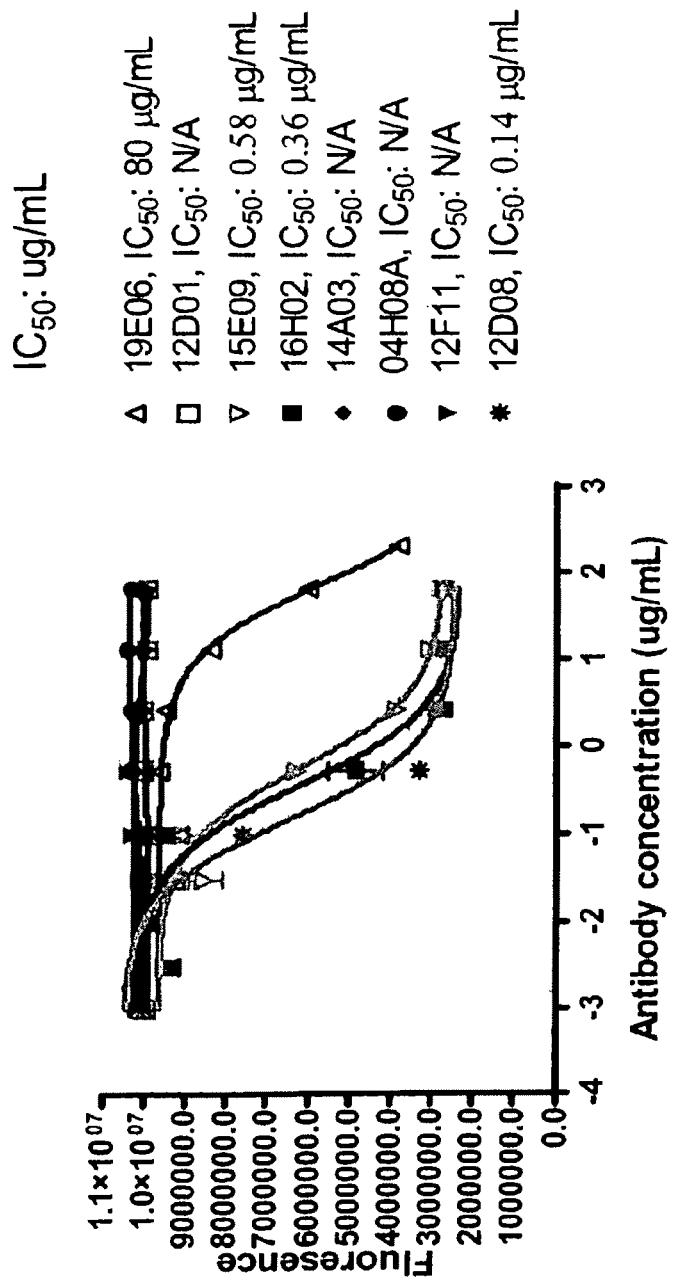
FIG. 1 illustrates inhibition of human TL1A (huTL1A)-induced Caspase activity on TF-1 cells by mouse and hamster anti-TL1A antibodies. Ab#1—19E06; Ab#2—12D01; Ab#3—15E09; Ab#4—16H02; Ab#5—14A03; Ab#6—04H08A; Ab#7—12F11; Ab#8—12D08.
Figure 2:
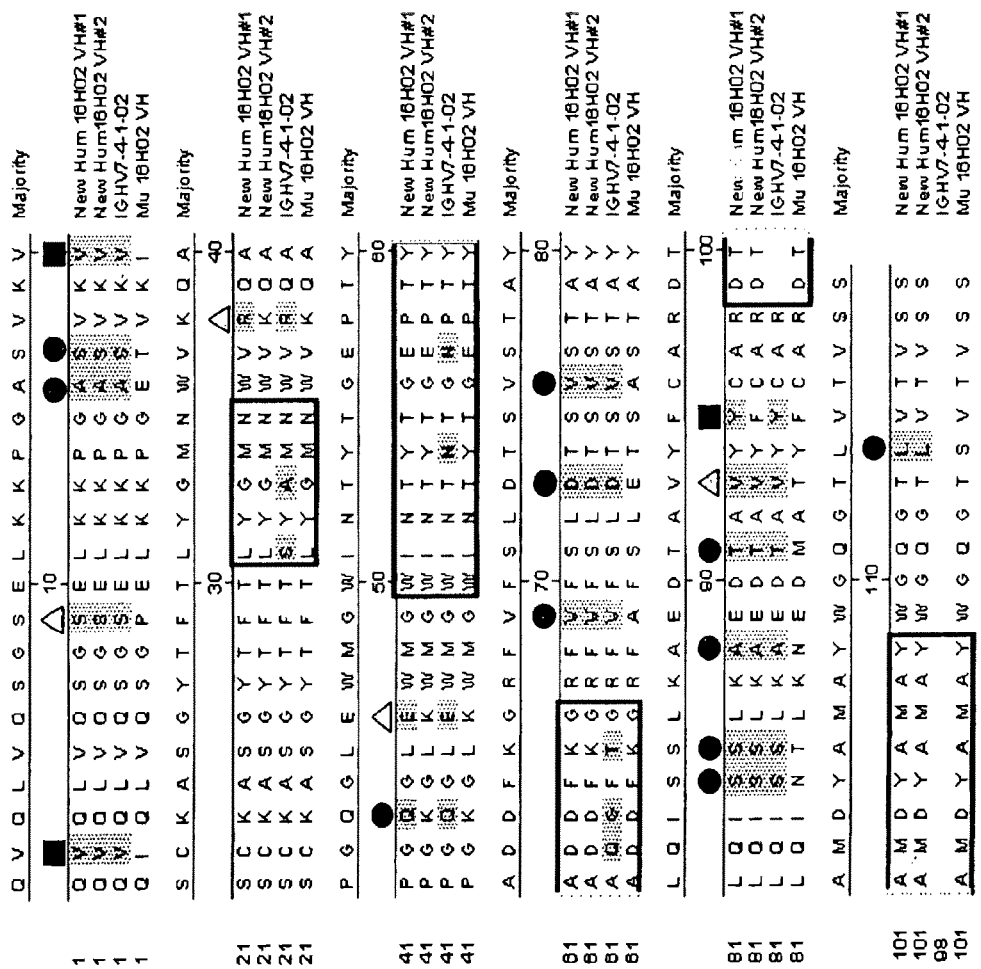
FIG. 2 illustrates an alignment of the VH Domain of mouse anti-TL1A 16H02 (SEQ ID NO: 70) with the closest human germline gene, IGHV7-4-1-02 (SEQ ID NO: 69). The alignment was used as a template to create 2 different versions of humanized 16H02 VH, identified in the figure as New Hum 16H02 VH#1 (SEQ ID NO: 21) and VH#2 (SEQ ID NO; 22).
Figure 4:
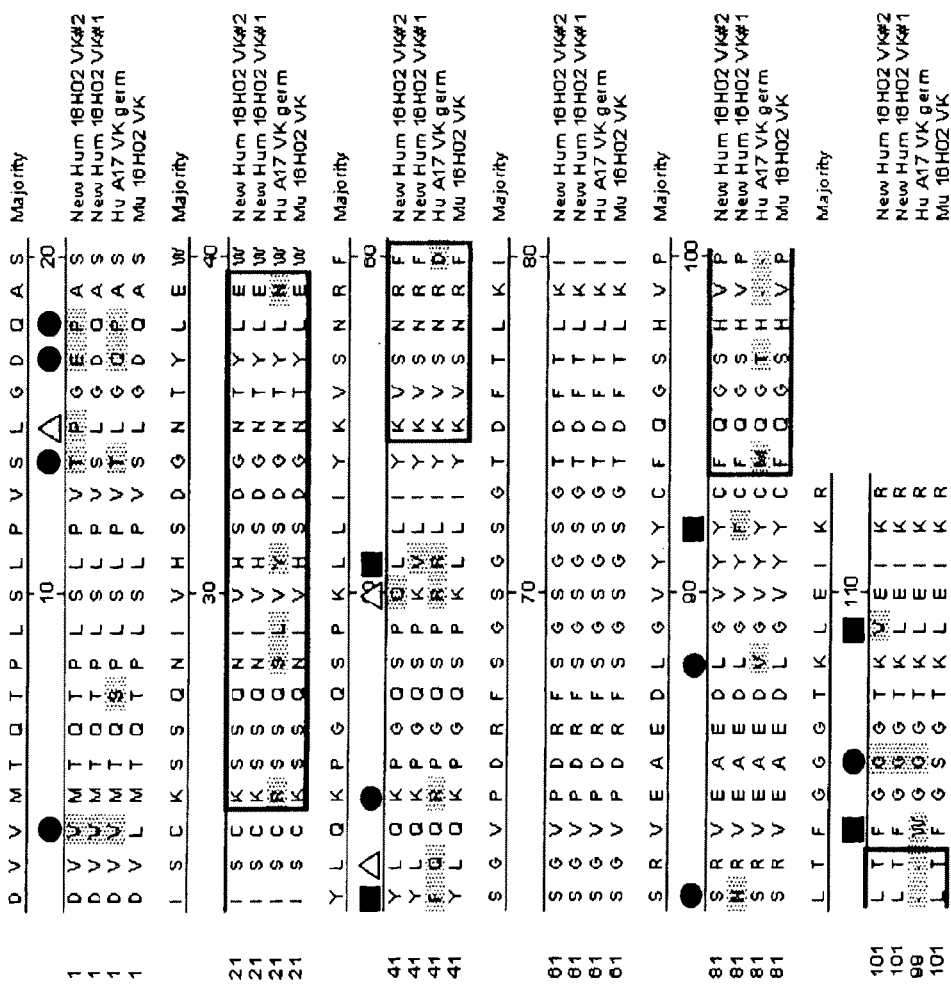
FIG. 4 illustrates an alignment of the VK domain of mouse anti-TL1A 16H02 (SEQ ID NO: 74) with the closest human germline gene, A17 (SEQ ID NO: 73). The alignment was used as a template to create 2 different versions of humanized 16H02 VH, identified in the figure as New Hum 16H02 VK#1 (SEQ ID NO: 72) and VK#2 (SEQ ID NO: 26).
Figure 7:
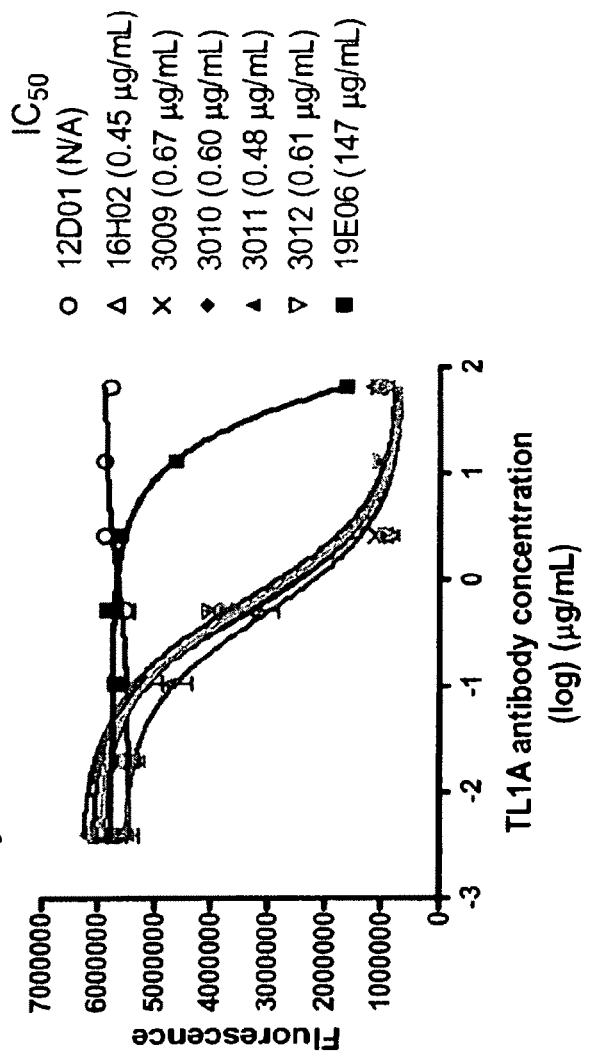
FIG. 7 illustrates the activity of 16H02 TL1A monoclonal antibodies after one round of humanization by showing the inhibition of TL1A-induced caspase activity in TF-1 cells by the humanized antibodies compared to mouse anti-TL1A antibody controls. 12D01=mouse anti-TL1a negative control; 16H02=mouse anti-TL1A positive control; 19E06=hamster anti-TL1A control; 3009=humanized anti TL1A 16H02 VH#1+VK#1; 3010=humanized anti TL1A 16H02 VH#2+VK#1; 3011=humanized anti TL1A 16H02 VH#1+VK#2; 3012=humanized anti TL1A 16H02 VH#2+VK#2.
Figure 8:
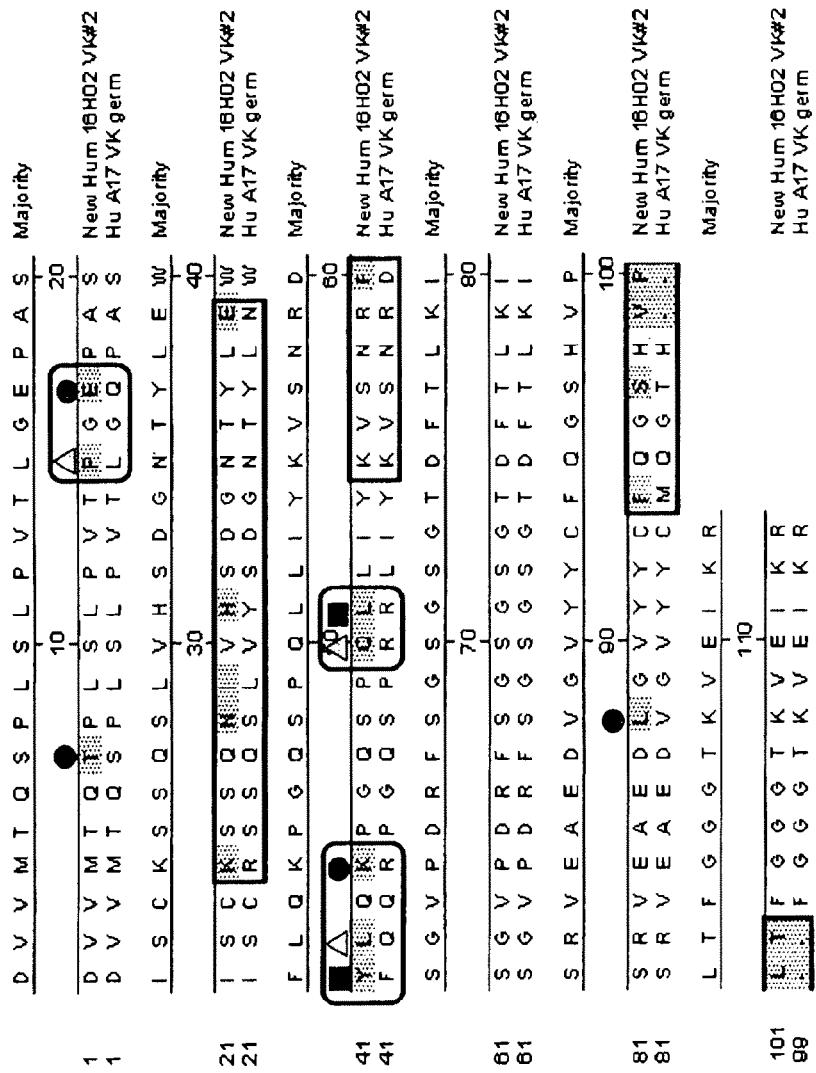
FIG. 8 illustrates the final mutations required for complete humanization of 16H02 VK framework. To create a fully humanized 16H02 light chain the New Hum16H02 VK#2 (SEQ ID NO: 26) (see FIG. 4) starting sequence was aligned with the A17 germline sequence (SEQ ID NO: 76) and 3 distinct regions or blocks identified (solid circles) for further mutagenesis. Synthetic light chains were constructed that contained all possible combinations of either the non-mutated wild type VK#2 sequence (=W) or A17 human germline sequence (=M) within each of the 3 regions or blocks.
Figure 10:
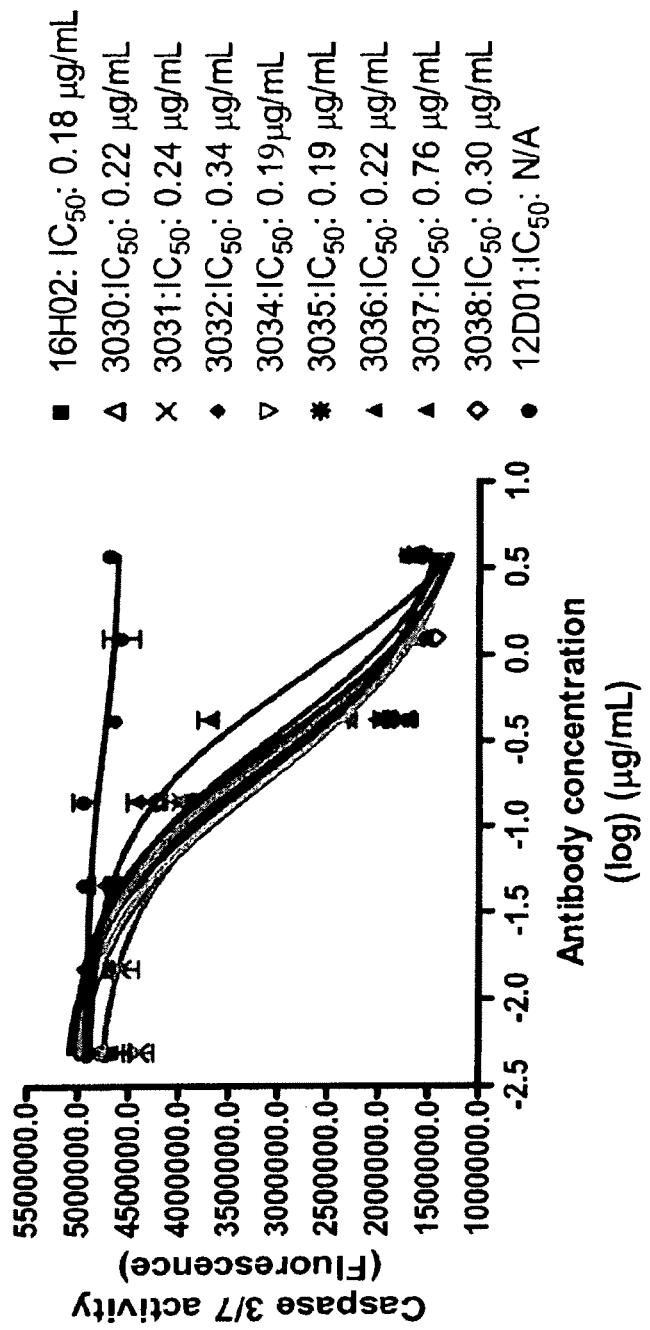
FIG. 10 illustrates inhibition of human TL1A (huTL1A)-induced Caspase activity on TF-1 cells by a panel of various humanized anti-TL1A antibodies from FIG. 9. Activity of a fully humanized 16H02 TL1A antibody identified as 3038 is compared to that of the original mouse anti-TL1A antibody 16H02.
Figure 15:
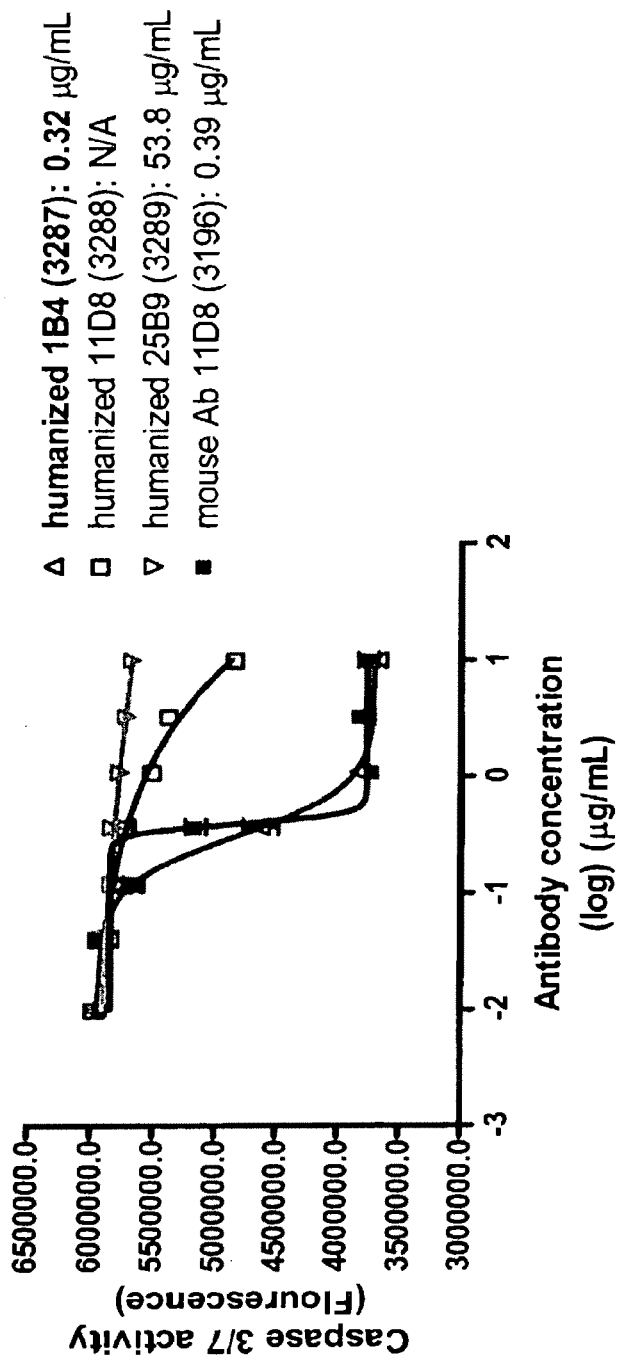
FIG. 15 illustrates the inhibition of mammalian derived TL1A-induced caspase activity in TF-1 cells by humanized TL1A antibodies (1B4, 11D8, 25B9) compared to the mouse 11D8 antibody.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, speigelmers, and diabodies. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), Fab HSA fusion polypeptides in which the VH-CH1 are produced as a fusion to HSA, which then folds with its cognate VK-CK light chain to form a Fab, and minimal recognition units consisting of the amino acid residues that mimic the hypervariable region.

A humanized antibody is a recombinant protein in which the CDRs from an antibody from one species, e.g., a rodent antibody, are transferred from the heavy and light variable chains of the rodent antibody into human heavy and light variable domains or heavy and light variable domains that have been mutagenized to include at least a portion of the amino acid sequence of the human heavy and light variable domains (as represented by "percent humanization"). The constant domains of the antibody molecule may be derived from those of a human antibody.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

As used herein, "CDR" means a "complementarity determining region" that is present in a variable domain of an antibody heavy chain (VH) or a variable domain of an antibody light chain (VL or VK). Each variable domain includes three CDRs which are designated CDR-H1, CDR-H2, and CDR-H3, for those present in the heavy chain variable domain, and CDR-L1, CDR-L2, and CDR-L3 for those present in the light chain variable domain. The Kabat numbering system is used herein. As such, CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Conjugation to a Therapeutic or Diagnostic Agent

The antigen-binding polypeptides disclosed herein may be conjugated or fused to a therapeutic agent, which may include radioactive labels, an immunomodulator, a hormone, a photoactive therapeutic agent, a cytotoxic agent, which may be a drug or a toxin, and a combination thereof. Drugs may include those drugs that possess the pharmaceutical property selected from the group consisting of antimitotic, antikinase, alkylating, antimetabolite, antibiotic, alkaloid, antiangiogenic, apoptotic agents and combinations thereof. More specifically, these drugs are selected from the group consisting of nitrogen mustards, ethylenimine derivatives, alkyl sulfonates, nitrosoureas, triazenes, folic acid analogs, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, anthracyclines, taxanes, and their analogs, and a combination thereof. The toxins encompassed by the present invention may be selected from the group consisting of ricin, abrin, alpha toxin, saporin, ribonuclease (RNase), e.g., onconase, DNase I, Staphylococcal enterotoxin-A, pokeweed antiviral protein, gelonin, diphtherin toxin. Pseudomonas exotoxin, and Pseudomonas endotoxin.

Immunomodulators may be selected from the group consisting of a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF)), interferon, such as interferons-alpha, -beta, or -gamma, and stem cell growth factor, such as designated "S1 factor". More specifically, immunomodulators may include IL-1, IL-2, IL-3, IL-6, IL-10, IL-12, IL-18, IL-21 interferon-gamma, TNF-alpha or a combination thereof.

The antigen-binding polypeptides disclosed herein may be conjugated or fused to a diagnostic agent. Diagnostic agents may include photoactive diagnostic agents or radiolabels having an energy between 60 and 4,000 keV, or a non-radioactive label. The radioactive label is preferably a gamma-, beta-, and positron-emitting isotope and is selected from the group consisting of $^{125}$I, $^{131}$I, $^{123}$I, $^{124}$I, $^{86}$Y, $^{186}$Re, $^{188}$Re, $^{62}$Cu, $^{64}$Cu, $^{111}$In, $^{67}$Ga, $^{68}$Ga, $^{99m}$Tc, $^{94m}$Tc, $^{18}$F, $^{11}$C, $^{13}$N, $^{15}$O, $^{76}$Br and combinations thereof. Diagnostic agents may include contrast agents, for example, such as manganese, iron or gadolinium.

Exemplary Method of Making Anti-TL1A Antibodies Using Hybridoma Technology

BALB/c mice can be immunized with recombinant TL1A protein (extracellular domain). In a typical procedure 10 mg of protein in 50 ml of complete Freund's adjuvant (Sigma) is injected subcutaneously. Two to four additional injections in incomplete Freund's adjuvant can be given at 2 week intervals followed by a final boost in PBS. Alternatively, injections can be given in the foot pads. Three days later mice can be sacrificed, their spleens or poplietal lymph nodes can be harvested and lymphocytes can be isolated for fusion. Lymphocytes can be fused with P3X63Ag8.653 plasmacytoma cells at 5:1 ratio using PEG/DMSO (Sigma) as a fusion agent. After fusion cells can be resuspended in selective HAT media and seeded at $10^6$ cells per well in 96 well plates. The supernatants from hybridomas that survived HAT selection can be screened by direct binding ELISA for the presence of TL1A binding antibodies. Hybridomas secreting TL1A binding antibodies can be identified and their supernatants can be further screened by inhibition of binding ELISA for antibodies inhibiting binding of TL1A to its receptor DR3. The hybridomas identified as positives for inhibition of TL1A binding can then be screened for inhibition of TL1A induced caspase activity in TF-1 cells to identify TL1A antagonistic clones.

Exemplary Antibody Humanization Strategy

One goal in humanizing the anti-TL1A antibodies is to obtain 70-100% humanized VH and VK domains that retain 90-100% of original binding affinity and specificity. Site-directed mutagenesis of individual high risk positions in VH and VK can be used to further humanize the antibodies while maintaining binding affinity and specificity.

Humanization can be performed by CDR grafting and structure based analysis and variable region resurfacing. (See Jones et al., NATURE (1986) May 29-Jun. 4; 321(6069):522-5; Roguska et al., PROTEIN ENGINEERING, 1996, 9(10):895-904; and Studnicka et al., Humanizing Mouse Antibody Frameworks While Preserving 3-D Structure. PROTEIN ENGINEERING, 1994, Vol. 7, pg 805). The primary antibody sequence and 3-D structure data can be utilized to identify key framework residues required to maintain the binding affinity and specificity. The "Blast for Ig sequences" website sponsored by the NCBI can be used to identify the closest match to the mouse VH and VK region used in the study. Human germline VH and VK genes can be chosen as the best matches to the mouse sequence VH and VK sequences. Alternatively, sequences from the naturally expressed human antibody repertoire can be used as a template for humanization either alone or in combination with the closest matching human germ line gene.

After aligning mouse anti-TL1A VH and VK to the nearest human germline or expressed repertoire of genes, the amino acid at every position can be evaluated for potential influence on binding and immunogenicity. This information can be used to assign a low, moderate, or high risk value for mutation at each position. In one embodiment, only the low and moderate risk positions are mutated while avoiding the high risk positions. If necessary, an affinity maturation strategy can be performed by incorporating tyrosines pair wise at each position in the CDR's of VH, VK or both.

Exemplary Cloning and Sequencing of Murine Anti-TL1A VH and VK Domains from Hybridoma Cell Lines Hybridoma cells can be pelleted, washed 3× with PBS and RNA extracted using Trizol reagent (Invitrogen, Cat. No. 15596-026) following the manufacturers protocol. Total RNA can be converted to cDNA using a 5' RACE kit (Rapid Amplification of cDNA Ends, Invitrogen, Cat. No. 18374-058) following the manufacturers protocol. Briefly, RNA can be ligated to random hexamer primer, Random N6, and 1$^{st}$ strand cDNA can be generated using superscript II RNAase H negative reverse transcriptase. The cDNA can be purified using a GlassMax spin cartridge provided with the kit and then reacted with TdT (terminal deoxynucleotidyl transferase) in the presence of dCTP to append the cDNA with C basepairs at the 5' end. The dC-tailed cDNA can be PCR amplified using an anchor primer specific for the dC tail and a gene specific primer that hybridizes to highly conserved DNA sequence in the mouse constant heavy 1 (CH1) for VH and constant kappa (CK) for VK. The resulting PCR product can be analyzed by gel electrophoresis for correct size corresponding to intact VH or VK domain then purified and ligated into a TOPO TA vector (Invitrogen Cat. No. K4575-01) following the manufacturers protocol. After transformation into bacteria DNA can be prepared from clones containing the correct size insert and the DNA sequence can be determined using a Big Dye terminator sequencing reaction mix (Applied Biosystems, Part No. 4336699) and a 3700 ABI/Prism DNA analyzer following manufacturers protocol.

Exemplary Humanizing Murine Anti-TL1A Antibodies

Murine anti-TL1A antibodies can be identified based on binding data and sequence data generated as described above. The amino acid sequence of the VH and VK domains from these antibodies can be aligned to human germline VH and VK domains using currently available public databases (i.e., Blast for IgG at the NCBI and V-base at the MRC). At those positions in the framework where the mouse sequence differed from the human germline, an iterative process can be used to convert or mutate the mouse framework so it matches the corresponding human germline framework. In addition, or alternatively, certain CDR amino acid residues for both the VH and VK can be mutated by replacement with tyrosine (i.e., affinity matured) to potentially help compensate for any losses in affinity due to the framework residues changes. The affinity matured and humanized mouse VH and VK domains can be generated by a polymerase chain reaction process using a panel of overlapping synthetic DNA oligonucleotides. As part of the synthetic gene design process a codon optimization strategy can be used, that is to say the triplet code for each amino acid that is preferentially utilized by mammalian cells for gene expression can be incorporated at each position. The synthetic VH and VK domains can be cloned into specialized mammalian expression vectors that allow the corresponding domains to be expressed in the context of a fully human IgG1, G4 or Kappa antibody backbone. Small-scale production of the humanized antibodies can be achieved by co-transfection of an IgG1 or G4 construct with the Kappa construct into 293F cells with lipofectamine (Invitrogen) following manufactures protocol. Supernatants from the transient transfections can be passed through Protein A or G resin and the IgG can be purified to homogeneity for testing in cell based assays.

The following examples are given to illustrate the present invention. It should be understood, however, that the invention is not to be limited to the specific conditions or details described in these examples. All published and/or publicly available documents described herein are specifically incorporated by reference.

Example 1

Amino Acid Sequences of VH and VK Domains of Mouse and Hamster anti-TL1A monoclonal antibodies prepared as described herein are shown below. The CDR regions of the variable domains are underlined.

```
12D08 VK (SEQ ID NO: 45):
DVLMTQTPLS LPVSLGDQAS ISCRSSQSIV HSNGNTYLDW

YLQKPGQSPN LLIYKVSNRF SGVPDRFSGS GSGTDFTLKI

SRVEAEDLGV YYCFQGSHVP LTFGAGTKLE LKR

16H02 VK (SEQ ID NO: 46):
DVLMTQTPLS LPVSLGDQAS ISCKSSQNIV HSDGNTYLEW

YLQKPGQSPK LLIYKVSNRF SGVPDRFSGS GSGTDFTLKI

SRVEAEDLGV YYCFQGSHVP LTFGSGTKLE IKR

15E09 VK (SEQ ID NO: 47):
ETTVTQSPAS LSMAIGEKVT IRCITSTDID DDMNWYQQKP

GEPPKLLISE GNTLRPGVPS RFSSSGYGTD FVFTIENMLS

EDVADYYCLQ SDNLPLTFGA GTKLELKR

19E06 VK (SEQ ID NO: 48):
DIVMTQSPSS LAVSTGGTVT LTCLSSQSLF SSDTNKNYLN

WYLQKPGQSP KLLVYHASTR LTGVPDRFIG SGSGTDFTLT

INSVQAEDLG DYYCQQHFRP PFTFGRGTKL EIKR

IB4 VK AA
                                (SEQ ID NO: 49)
QIVLTQSPAIMSASLGAEITLTCSASSSVNYMHWYQQRSGTSP

KLLIYSTSNLASGVPSRFSGSGSGTFYSLTISSVEAEDAADYY

CHQWNNYGTFGGGTKLEIKR

25B9 VK AA
                                (SEQ ID NO: 50)
ENVLTQSPAILAASLGQKVTMTCSASSSVSSGYLHWYQQKSGA

SPKPLIHRTSNLASGVPPRFSGSGSGTSYSLSISSVEAEDDAT

YYCQQWSGFPFTFGSGTKLEIKR

27A8 VK AA
                                (SEQ ID NO: 51)
DIVLTQSPASLTVSLGQRATISCRASQNVSTSSYSHMHWSQQK

PGQPPKLLIKYASNLDSGVPARFSGSGSGTDFTLNIHPVEEED

IATYYCQHSWEIPYTEGGGTKLHKR

11D8 VK AA
                                (SEQ ID NO: 52)
DIVMTQSPASLTVSLGQRATISCRASQSVSTSSYSHMHWYQQK

PGQPPKLLIRYASNLESGVPARFSGSGSGTDFTENIHPVEEED

TAIYYCQHSWELPYTEGGGTKLEIKR
```

38D6 VK AA (SEQ ID NO: 53)
DIVLTQFPASLPVSLGQRATISCRASQSVSTSSYSHMHWYQQK

PGQPPKLLITYASNLDSGVPARISGSGSGTDFTLNIHPVEEED

TATYYCHHSWELPYTFGGGTKLEIKR

12D08 VH (SEQ ID NO: 54):
QIQLVQSGPE LKKPGETVKI SCKASGYTFT NYGMNWVKQA

PGKGLKWMGW INTYTGEPTY ADDFKGRFAF SLETSASTAY

LQINNLKNED MATYFCAKDY GKYGDYYAMD YWGQGTSVTV

SS

16H02 VH (SEQ ID NO: 55):
QIQLVQSGPE LKKPGETVKI SCKASGYTFT LYGMNWVKQA

PGKGLKWMGW INTYTGEPTY ADDFKGRFAF SLETSASTAY

LQINTLKNED MATYFCARDT AMDYAMAYWG QGTSVTVSS

15E09 VH (SEQ ID NO: 56):
EVKLVDSGGG LVQPGDSLRL SCATSGFTFS DFYMEWVRQP

PGKRLEWIAA SGNKANDYTT EYSASVKGRF IVSRDTSQSI

LYLQMNDLRA EDTAIYYCVR DAGYGYWYFD VWGAGTTVTV

SS

19E06 VH (SEQ ID NO: 57):
QIQLQESGPS LVKPSQSLSL TCSVTGYSIT SDSYWNWIRQ

FPGKNLVWMG YISYRGSTNY NPSLKSRISI TRDTSRNQFF

LQLNSVTTED TATYYCARYS GYSFWYFDFW GQGTQVTVSS

1B4 VH (SEQ ID NO: 58)
a. QVTLKESGPGILQPSQTLSLTCSFSGFSLTTSNMGVVWIR

QPSGKGLEWLLHILWDDREYSNPALKSRLTISKDPFNNQVFLK

IANVDTADTATYYCARMSRNYYGSSYVMDYWGQGTSVTVSS

25B9 VH (SEQ ID NO: 59)
EVQLQQSGPELVKPGASVKMSCKASGYTFTSYVMHWVKQKTGQ

GLEWIGYINSNNDGTKYNEKFKGKATLTSDKSSSTAYMELSSL

TSEDSAVYYCATGDYYGGTSYWYFDVWGAGTTVTVSS

11D8 VH (SEQ ID NO: 60)
EVQLQQSGPELEKPGASVKISCKASGYSFTGYNMNWVKQSNGK

SLEWIGNIDPYFGDTNYNQNFKGRATLTVDKSSNTAYMQLMSL

TSEDSAVYYCAREGAARAKNYFDYWGQGTTLTVSS

27A8 VH (SEQ ID NO: 61)
EVQLQQSGPELETPGASVKISCKASGYSFTGYNMNWVKQTNGK

SLEWIGNIDPYFGDANYNRKFKGKATLTVDKSSSTAYMQLRSL

TSEDSAVYYCAKEGAARAKNYFDYWGQGTTLTVSS

38D6 VH AA (SEQ ID NO: 62)
EVQLQQSGPELEKPGASVKISCKASGYSFTGYNMNWVRQTNGK

SLEWIGHIDPYYGDATYRQKFKGKATLTVDKSSNTAYMQLKSL

TSEDSAVYFCAREGAARARNYFDYWGQGTTLTVSS

Example 2

This example describes an assay protocol to measure inhibition of TL A-induced caspase activity on TF-1 cells.

To determine neutralizing activity of anti-TL1A antibodies, their effects on TL1A-induced caspase activity in TF-1 cells were determined. See FIG. 1. TF-1 cells were seeded at 75,000 cells/well in a black 96-well plate with clear bottom in RPMI medium containing 1% fetal bovine serum. Cells were treated with 10 µg/mL cyclohexamide and 100 ng/mL TL1A in the absence or presence of various concentrations of mouse or hamster parental TL1A antibodies for 6 hr at 37° C. Caspase activity was measured by Apo-One homogeneous caspase-3/7 assay kit (Promega). Equal volume of Apo-One homogeneous caspase-3/7 assay buffer containing caspase substrate, Z-DEVD-Rhodamine (SEQ ID NO: 63) was added to each well containing cells. After overnight incubation, fluorescence was measured by a Wallac Victor2 fluorescence plate reader with excitation filter 485 nm and emission filter 535 nm.

The results, shown in FIG. 1, shows that the level of fluorescence, which correlates with caspase activity, decreases with increasing concentration of four (4) different anti-TL1A antibodies: Ab#1—19E06; Ab#3—15E09; Ab#4—16H02; and Ab#8—12D08.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

The invention claimed is:

1. An isolated polynucleotide encoding an antigen-binding polypeptide that binds to specifically to TL1A, comprising:
   (a) a humanized heavy chain variable region comprising:
      (1) a CDR-H1 comprises the amino acid sequence selected from the group consisting of LYGMN (SEQ ID NO:11), NYGMN (SEQ ID NO:12), and TSN-MGVV (SEQ ID NO:7);
      (2) a CDR-H2 comprises the amino acid sequence of (WINTYTGEPTYADDFKG) (SEQ ID NO:13) or HILWDDREYSNPALKS (SEQ ID NO:8); and
      (3) a CDR-H3 comprises the amino acid sequence selected from the group consisting of DTAM-DYAMAY (SEQ ID NO:14), DYGKYGDYYAMDY (SEQ ID NO:15), and MSRNYYGSSYVMDY (SEQ ID NO:9); and/or
   (b) a humanized light chain variable region comprising:
      (1) a CDR-L1 comprises the amino acid sequence selected from the group consisting of KSSQNIVHS-DGNTYLE (SEQ ID NO:16), RSSQSIVHSNGN-TYLD (SEQ ID NO:17) and SASSSVNYMH (SEQ ID NO:35);
      (2) a CDR-L2 comprises the amino acid sequence of KVSNRFS (SEQ ID NO:18) or STSNLAS (SEQ ID NO:36); and
      (3) a CDR-L3 comprises the amino acid sequence of FQGSHVPLT (SEQ ID NO:19) or HQWNNYGT (SEQ ID NO:37).

2. The polynucleotide of claim 1, wherein the humanized heavy chain variable region comprises the amino acid sequence of:

(SEQ ID NO: 10)
QVTLKESGPALVKPTQTLTLTCTFSGFSLSTSNNIGVVWIRQPPGKAL

EWLAHILWDDREYSNPALKSRLTISKDTSKNQVVLTMTNMDPVDTATY

YCARMSRNYYGSSYVMDYWGQGTLVTVSS.

3. The polynucleotide of claim 1, wherein the humanized heavy chain variable region comprises an amino acid sequence selected from the group consisting of:

(a)
(SEQ ID NO: 21)
QVQLVQSGSELKKPGASVKVSCKASGYTFTLYGMNWVRQAPGQGLEW

MGWINTYTGEPTYADDFKGRFVFSLDTSVSTAYLQISSLKAEDTAVY

YCARDTAMDYAMAYWGQGTLVTVSS;

(b)
(SEQ ID NO: 22)
QVQLVQSGSELKKPGASVKVSCKASGYTFTLYGMNWVKQAPGKGLKW

MGWINTYTGEPTYADDFKGRFVFSLDTSVSTAYLQISSLKAEDTAVY

FCARDTAMDYAMAYWGQGTLVTVSS;

(c)
(SEQ ID NO: 23)
QVQLVQSGSELKKPGASVKVSCKASGYTFTNYGMNWVRQAPGQGLE

WMGWINTYTGEPTYADDFKGRFVFSLDTSVSTAYLQISSLKAEDTA

VYYCARDYGKYGDYYAMDYWGQGTLVTVSS;
and (d)
(SEQ ID NO: 24)
QVQLVQSGSELKKPGASVKVSCKASGYTFTNYGMNWVRQAPGKGLKW

MGWINTYTGEPTYADDFKGRFVFSLDTSVSTAYLQISSLKAEDTAVY

FCARDYGKYGDYYAMDYWGQGTLVTVSS.

4. The polynucleotide of claim 1, wherein the humanized light chain variable region comprises the amino acid sequence of:

```
                                              (SEQ ID NO: 38)
DIQLTQSPSFLSASVGDRVTITCSASSSVNYMHWYQQKPGKAPKLLIYST

SNLASGVPSRFSGSGSGTEFTLTISSLQPEDFATYYCHQWNNYGTFGQGT

KVEIKR.
```

5. The polynucleotide of claim 1, wherein the humanized light chain variable region comprises an amino acid sequence selected from the group consisting of

```
(a)
                                              (SEQ ID NO: 27)
DVVMTQSPLSLPVTLGQPASISCKSSQNIVHSDGNTYLEWFQQRPGQSP

RRLIYKVSNRFSGVPDRFSGSGSGTDFTLKISRVEAEDVGVYYCFQGSH

VPLTFGGGTKVEIKR;

(b)
                                              (SEQ ID NO: 28)
DVVMTQSPLSLPVTLGQPASISCKSSQNIVHSDGNTYLEWFQQRPGQSP

RRLIYKVSNRFSGVPDRFSGSGSGTDFTLKISRVEAEDVGVYYCFQGSH

VPLTFGQGTKVEIKR;

(c)
                                              (SEQ ID NO: 26)
DVVMTQTPLSLPVTPGEPASISCKSSQNIVHSDGNTYLEWYLQKPGQSP

QLLIYKVSNRFSGVPDRFSGSGSGTDFTLKISRVEAEDLGVYYCFQGSH

VPLTFGGGTKVEIKR;

(d)
                                              (SEQ ID NO: 66)
DVVMTQTPLSLPVSLGDQASISCKSSQNIVHSDGNTYLEWYLQKPGQSP

KVLIYKVSNRFSGVPDRFSGSGSGTDFTLKISRVEAEDLGVYYCFQGSH

VPLTFGGGTKVEIKR;

(e)
                                              (SEQ ID NO: 41)
DVVMTQSPLSLPVTLGQPASISCRSSQSIVHSNGNTYLDWFQQRPGQSP

RRLIYKVSNRFSGVPDRFSGSGSGTDFTLKISRVEAEDVGVYYCFQGSH

VPLTFGGGTKVEIKR;

(f)
                                              (SEQ ID NO: 42)
DVVMTQSPLSLPVTLGQPASISCRSSQSIVHSNGNTYLDWFQQRPGQSP

RRLIYKVSNRFSGVPDRFSGSGSGTDFTLKISRVEAEDVGVYYCFQGSH

VPLTFGQGTKVEIKR;

(g)
                                              (SEQ ID NO: 43)
DVVMTQTPLSLPVTPGEPASISCRSSQSIVFISNGNTYLDWYLQKPGQ

SPQLLIYKVSNRFSGVPDRFSGSGSGTDFTLKISRVEAEDLGVYYCFQG

SHVPLTFGGGTKVEIKR;
and (h)
                                              (SEQ ID NO: 44)
DVVMTQTPLSLPVSLGDQASISCRSSQSIVHSNGNTYLDWYLQKPGQSP

KVLIYKVSNRFSGVPDRFSGSGSGTDFTLKINRVEAEDLGVYFCFQGSH

VPLTFGGGTKLEIKR.
```

6. The polynucleotide of claim 1, wherein the polynucleotide encodes an antigen-binding polypeptide comprising:

(a) a humanized heavy chain variable region comprising an amino acid sequence selected from the group consisting of:
  (i) SEQ ID NO:10;
  (ii) SEQ ID NO:21;
  (iii) SEQ ID NO:22;
  (iv) SEQ ID NO:23; and
  (v) SEQ ID NO:24; and/or
(b) a humanized light chain variable region comprising an amino acid sequence selected from the group consisting of:
  (i) SEQ ID NO:38;
  (ii) SEQ ID NO:27;
  (iii) SEQ ID NO:28;
  (iv) SEQ ID NO:26;
  (v) SEQ ID NO:66;
  (vi) SEQ ID NO:41;
  (vii) SEQ ID NO:42;
  (viii) SEQ ID NO:43; and
  (ix) SEQ ID NO:44.

7. The polynucleotide of claim 6, wherein the polynucleotide encodes an antigen-binding polypeptide comprising:
  (a) a humanized variable light chain region comprising the amino acid sequence of:

```
                                              (SEQ ID NO: 38)
DIQLTQSPSFLSASVGDRVTITCSASSSVNYMHWYQQKPGKAPKLLI

YSTSNLASGVPSRFSGSGSGTEFTLTISSLQPEDFATYYCHQWNNYG

TFGQGTKVEIKR;
and/or
```

(b) a humanized variable heavy chain region comprising the sequence of:

```
                                              (SEQ ID NO: 10)
QVTLKESGPALVKPTQTLTLTCTFSGFSLSTSNMGVVWIRQPPGKAL

EWLAHILWDDREYSNPALKSRLTISKDTSKNQVVLTMTNMDPVDTAT

YYCARMSRNYYGSSYVMDYWGQGTLVTVSS.
```

8. The polynucleotide of claim 1, wherein the polynucleotide encodes an antigen-binding polypeptide selected from the group consisting of an antibody molecule, a Fab fragment, a Fab' fragment, a F(ab')2 fragment, and an scFv molecule.

9. The polynucleotide of claim 8, wherein the polypeptide is an antibody molecule.

10. The polynucleotide of claim 9, wherein the antibody is a chimeric antibody comprising a humanized heavy chain constant region and a humanized light chain constant region.

11. The polynucleotide of claim 9, wherein the antibody is an IgG molecule.

12. The polynucleotide of claim 8, wherein the polypeptide is an scFv molecule.

13. The polynucleotide of claim 12, wherein the scFv molecule has a formula selected from the group consisting of NH2-L-VH-X-VK-COOH and NH2-L-VK-X-VH-COOH, wherein:
  (a) L is a leader sequence;
  (b) VH is the humanized antibody heavy chain variable region;
  (c) X is a linking polypeptide; and
  (d) VK is the humanized antibody light chain variable region.

14. The polynucleotide of claim 8, wherein the polypeptide is a Fab HSA fusion molecule.

15. The polynucleotide of claim 14, wherein the Fab HSA fusion molecule has a formula selected from the group consisting of NH2-VH-CH1-HSA-COOH and NH2-HSA-CH1-VH-COOH combined with NH2-VK-CK-COOH, wherein VH-CH1-HSA or HSA-CH1-VH is the humanized antibody heavy chain variable region (VH) and human constant heavy chain domain 1 (CH1) produced as a fusion protein with human serum albumin (HSA) which folds with its cognate humanized antibody light chain variable region (VK) and human constant kappa domain (CK) to form the Fab-HSA or HSA-Fab fusion protein.

16. The polynucleotide of claim 1, wherein the polynucleotide encodes an antigen-binding polypeptide conjugated to a therapeutic or diagnostic agent.

17. The polynucleotide of claim 16, wherein:
    (a) the therapeutic agent is selected from the group consisting of a cytotoxic agent, a radioactive label, an immunomodulator, a hormone, an enzyme, an oligonucleotide, a photoactive therapeutic agent or a combination thereof; or
    (b) the diagnostic agent is selected from the group consisting of a radioactive label, a photoactive diagnostic agent, an ultrasound-enhancing agent or a non-radioactive label.

18. The polynucleotide of claim 1, wherein the polypeptide binds to TL1A with an affinity constant of at least about 106M-1.

19. The polynucleotide of claim 1, wherein the polypeptide is encoded by cDNA.

20. A recombinant polynucleotide comprising a promoter sequence operably linked to the polynucleotides of claim 1.

21. An isolated cell transformed with the polynucleotide of claim 20.

22. A method of producing the polypeptide encoded by the recombinant polynucleotide of claim 20, the method comprising:
    (a) culturing a cell transformed with the recombinant polynucleotide to express the encoded polypeptide; and
    (b) recovering the polypeptide so expressed.

\* \* \* \* \*

SEQUENCE LISTING

```
<160> NUMBER OF SEQ ID NOS: 79

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Ser or Asn
<220> FEATURE:
<221> NAME/KEY: MOD_RES
```

```
<222> LOCATION: (3)..(3)
<223> OTHER INFORMATION: Gly or Ala

<400> SEQUENCE: 1

Xaa Tyr Xaa Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Tyr or Asn
<220> FEATURE:
<221> NAME/KEY: MOD_RES
<222> LOCATION: (8)..(8)
<223> OTHER INFORMATION: Glu or Asn
<220> FEATURE:
<221> NAME/KEY: MOD_RES
<222> LOCATION: (13)..(13)
<223> OTHER INFORMATION: Asp or Gln
<220> FEATURE:
<221> NAME/KEY: MOD_RES
<222> LOCATION: (14)..(14)
<223> OTHER INFORMATION: Asp or Gly
<220> FEATURE:
<221> NAME/KEY: MOD_RES
<222> LOCATION: (16)..(16)
<223> OTHER INFORMATION: Lys or Thr

<400> SEQUENCE: 2

Trp Ile Asn Thr Xaa Thr Gly Xaa Pro Thr Tyr Ala Xaa Xaa Phe Xaa
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr or Tyr
<220> FEATURE:
<221> NAME/KEY: MOD_RES
<222> LOCATION: (3)..(3)
<223> OTHER INFORMATION: Ala or Gly
<220> FEATURE:
<221> NAME/KEY: MOD_RES
<222> LOCATION: (4)..(4)
<223> OTHER INFORMATION: Met or Lys
<220> FEATURE:
<221> NAME/KEY: MOD_RES
<222> LOCATION: (5)..(5)
<223> OTHER INFORMATION: Asp or Tyr
<220> FEATURE:
<221> NAME/KEY: MOD_RES
<222> LOCATION: (6)..(6)
<223> OTHER INFORMATION: Tyr or Gly
<220> FEATURE:
<221> NAME/KEY: MOD_RES
<222> LOCATION: (7)..(7)
<223> OTHER INFORMATION: Ala or Asp
<220> FEATURE:
<221> NAME/KEY: MOD_RES
<222> LOCATION: (8)..(8)
```

```
<223> OTHER INFORMATION: Met or Tyr
<220> FEATURE:
<221> NAME/KEY: MOD_RES
<222> LOCATION: (9)..(9)
<223> OTHER INFORMATION: Ala or Tyr
<220> FEATURE:
<221> NAME/KEY: MOD_RES
<222> LOCATION: (10)..(10)
<223> OTHER INFORMATION: Tyr or Ala

<400> SEQUENCE: 3

Asp Xaa Xaa Xaa Xaa Xaa Xaa Xaa Xaa Xaa Met Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (5)..(5)
<223> OTHER INFORMATION: Asn or Ser
<220> FEATURE:
<221> NAME/KEY: MOD_RES
<222> LOCATION: (6)..(6)
<223> OTHER INFORMATION: Ile or Leu
<220> FEATURE:
<221> NAME/KEY: MOD_RES
<222> LOCATION: (8)..(8)
<223> OTHER INFORMATION: His or Tyr
<220> FEATURE:
<221> NAME/KEY: MOD_RES
<222> LOCATION: (10)..(10)
<223> OTHER INFORMATION: Asp or Asn
<220> FEATURE:
<221> NAME/KEY: MOD_RES
<222> LOCATION: (16)..(16)
<223> OTHER INFORMATION: Glu, Asn or Asp

<400> SEQUENCE: 4

Xaa Ser Ser Gln Xaa Xaa Val Xaa Ser Xaa Gly Asn Thr Tyr Leu Xaa
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phe or Asp

<400> SEQUENCE: 5

Lys Val Ser Asn Arg Xaa Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Phe or Met
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (6)..(9)
<223> OTHER INFORMATION: May or may not be present

<400> SEQUENCE: 6

Xaa Gln Gly Xaa His Val Pro Leu Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Ser Asn Met Gly Val Val
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Ile Leu Trp Asp Asp Arg Glu Tyr Ser Asn Pro Ala Leu Lys Ser
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Ser Arg Asn Tyr Tyr Gly Ser Ser Tyr Val Met Asp Tyr
1               5                   10

<210> SEQ ID NO 10
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Asn Met Gly Val Val Trp Ile Arg Gln Pro Pro Gly Lys Ala Leu Glu
        35                  40                  45
```

```
Trp Leu Ala His Ile Leu Trp Asp Asp Arg Glu Tyr Ser Asn Pro Ala
         50                  55                  60

Leu Lys Ser Arg Leu Thr Ile Ser Lys Asp Thr Ser Lys Asn Gln Val
 65              70                  75                  80

Val Leu Thr Met Thr Asn Met Asp Pro Val Thr Ala Thr Tyr Tyr
                 85                  90                  95

Cys Ala Arg Met Ser Arg Asn Tyr Tyr Gly Ser Ser Tyr Val Met Asp
            100                 105                 110

Tyr Trp Gly Gln Gly Thr Leu Val Thr Val Ser Ser
            115                 120
```

```
<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Tyr Gly Met Asn
 1               5
```

```
<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Tyr Gly Met Asn
 1               5
```

```
<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Ile Asn Thr Tyr Thr Gly Glu Pro Thr Tyr Ala Asp Asp Phe Lys
 1               5                  10                  15

Gly
```

```
<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Thr Ala Met Asp Tyr Ala Met Ala Tyr
 1               5                  10
```

```
<210> SEQ ID NO 15
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 15

Asp Tyr Gly Lys Tyr Gly Asp Tyr Tyr Ala Met Asp Tyr
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Ser Ser Gln Asn Ile Val His Ser Asp Gly Asn Thr Tyr Leu Glu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Ser Gln Ser Ile Val His Ser Asn Gly Asn Thr Tyr Leu Asp
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Val Ser Asn Arg Phe Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Gln Gly Ser His Val Pro Leu Thr
1               5

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
```

```
<222> LOCATION: (9)..(9)
<223> OTHER INFORMATION: Ser or Pro
<220> FEATURE:
<221> NAME/KEY: MOD_RES
<222> LOCATION: (16)..(16)
<223> OTHER INFORMATION: Ala or Glu
<220> FEATURE:
<221> NAME/KEY: MOD_RES
<222> LOCATION: (17)..(17)
<223> OTHER INFORMATION: Ser or Thr
<220> FEATURE:
<221> NAME/KEY: MOD_RES
<222> LOCATION: (20)..(20)
<223> OTHER INFORMATION: Val or Ile
<220> FEATURE:
<221> NAME/KEY: MOD_RES
<222> LOCATION: (31)..(31)
<223> OTHER INFORMATION: Leu, Ser or Asn
<220> FEATURE:
<221> NAME/KEY: MOD_RES
<222> LOCATION: (33)..(33)
<223> OTHER INFORMATION: Gly or Ala
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (43)..(43)
<223> OTHER INFORMATION: Gln or Lys
<220> FEATURE:
<221> NAME/KEY: MOD_RES
<222> LOCATION: (46)..(46)
<223> OTHER INFORMATION: Glu or Lys
<220> FEATURE:
<221> NAME/KEY: MOD_RES
<222> LOCATION: (54)..(54)
<223> OTHER INFORMATION: Tyr or Asn
<220> FEATURE:
<221> NAME/KEY: MOD_RES
<222> LOCATION: (57)..(57)
<223> OTHER INFORMATION: Glu or Asn
<220> FEATURE:
<221> NAME/KEY: MOD_RES
<222> LOCATION: (62)..(62)
<223> OTHER INFORMATION: Asp or Gln
<220> FEATURE:
<221> NAME/KEY: MOD_RES
<222> LOCATION: (63)..(63)
<223> OTHER INFORMATION: Asp or Gly
<220> FEATURE:
<221> NAME/KEY: MOD_RES
<222> LOCATION: (65)..(65)
<223> OTHER INFORMATION: Lys or Thr
<220> FEATURE:
<221> NAME/KEY: MOD_RES
<222> LOCATION: (69)..(69)
<223> OTHER INFORMATION: Val or Ala
<220> FEATURE:
<221> NAME/KEY: MOD_RES
<222> LOCATION: (73)..(73)
<223> OTHER INFORMATION: Asp or Glu
<220> FEATURE:
<221> NAME/KEY: MOD_RES
<222> LOCATION: (76)..(76)
<223> OTHER INFORMATION: Val or Ala
<220> FEATURE:
<221> NAME/KEY: MOD_RES
<222> LOCATION: (84)..(84)
<223> OTHER INFORMATION: Ser or Asn
<220> FEATURE:
<221> NAME/KEY: MOD_RES
<222> LOCATION: (85)..(85)
<223> OTHER INFORMATION: Ser or Thr
<220> FEATURE:
<221> NAME/KEY: MOD_RES
<222> LOCATION: (88)..(88)
<223> OTHER INFORMATION: Ala or Asn
<220> FEATURE:
```

```
<221> NAME/KEY: MOD_RES
<222> LOCATION: (91)..(91)
<223> OTHER INFORMATION: Thr or Met
<220> FEATURE:
<221> NAME/KEY: MOD_RES
<222> LOCATION: (93)..(93)
<223> OTHER INFORMATION: Val or Thr
<220> FEATURE:
<221> NAME/KEY: MOD_RES
<222> LOCATION: (95)..(95)
<223> OTHER INFORMATION: Tyr or Phe
<220> FEATURE:
<221> NAME/KEY: MOD_RES
<222> LOCATION: (100)..(100)
<223> OTHER INFORMATION: Thr or Tyr
<220> FEATURE:
<221> NAME/KEY: MOD_RES
<222> LOCATION: (101)..(101)
<223> OTHER INFORMATION: Ala or Gly
<220> FEATURE:
<221> NAME/KEY: MOD_RES
<222> LOCATION: (102)..(102)
<223> OTHER INFORMATION: Met or Lys
<220> FEATURE:
<221> NAME/KEY: MOD_RES
<222> LOCATION: (103)..(103)
<223> OTHER INFORMATION: Asp or Tyr
<220> FEATURE:
<221> NAME/KEY: MOD_RES
<222> LOCATION: (104)..(104)
<223> OTHER INFORMATION: Tyr or Gly
<220> FEATURE:
<221> NAME/KEY: MOD_RES
<222> LOCATION: (105)..(105)
<223> OTHER INFORMATION: Ala or Asp
<220> FEATURE:
<221> NAME/KEY: MOD_RES
<222> LOCATION: (106)..(106)
<223> OTHER INFORMATION: Met or Tyr
<220> FEATURE:
<221> NAME/KEY: MOD_RES
<222> LOCATION: (107)..(107)
<223> OTHER INFORMATION: Ala or Tyr
<220> FEATURE:
<221> NAME/KEY: MOD_RES
<222> LOCATION: (108)..(108)
<223> OTHER INFORMATION: Tyr or Ala
<220> FEATURE:
<221> NAME/KEY: MOD_RES
<222> LOCATION: (117)..(117)
<223> OTHER INFORMATION: Leu or Ser

<400> SEQUENCE: 20

Gln Xaa Gln Leu Val Gln Ser Gly Xaa Glu Leu Lys Lys Pro Gly Xaa
1               5                   10                  15

Xaa Val Lys Xaa Ser Cys Lys Ala Ser Gly Tyr Thr Phe Thr Xaa Tyr
            20                  25                  30

Xaa Met Asn Trp Val Xaa Gln Ala Pro Gly Xaa Gly Leu Xaa Trp Met
        35                  40                  45

Gly Trp Ile Asn Thr Xaa Thr Gly Xaa Pro Thr Tyr Ala Xaa Xaa Phe
50                  55                  60

Xaa Gly Arg Phe Xaa Phe Ser Leu Xaa Thr Ser Xaa Ser Thr Ala Tyr
65                  70                  75                  80

Leu Gln Ile Xaa Xaa Leu Lys Xaa Glu Asp Xaa Ala Xaa Tyr Xaa Cys
                85                  90                  95

Ala Arg Asp Xaa Xaa Xaa Xaa Xaa Xaa Xaa Xaa Met Asp Tyr Trp
            100                 105                 110

Gly Gln Gly Thr Xaa Val Thr Val Ser Ser
        115                 120
```

```
<210> SEQ ID NO 21
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Leu Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Thr Ala Met Asp Tyr Ala Met Ala Tyr Trp Gly Gln Gly
                100                 105                 110

Thr Leu Val Thr Val Ser Ser
        115

<210> SEQ ID NO 22
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Leu Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Thr Ala Met Asp Tyr Ala Met Ala Tyr Trp Gly Gln Gly
                100                 105                 110

Thr Leu Val Thr Val Ser Ser
        115

<210> SEQ ID NO 23
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23
```

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Lys Tyr Gly Asp Tyr Tyr Ala Met Asp Tyr Trp
                100                 105                 110

Gly Gln Gly Thr Leu Val Thr Val Ser Ser
        115                 120
```

<210> SEQ ID NO 24
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Tyr Gly Lys Tyr Gly Asp Tyr Tyr Ala Met Asp Tyr Trp
                100                 105                 110

Gly Gln Gly Thr Leu Val Thr Val Ser Ser
        115                 120
```

<210> SEQ ID NO 25
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (14)..(14)
<223> OTHER INFORMATION: Thr or Ser
<220> FEATURE:
<221> NAME/KEY: MOD_RES
<222> LOCATION: (15)..(15)

```
<223> OTHER INFORMATION: Pro or Leu
<220> FEATURE:
<221> NAME/KEY: MOD_RES
<222> LOCATION: (17)..(17)
<223> OTHER INFORMATION: Glu, Asp or Gln
<220> FEATURE:
<221> NAME/KEY: MOD_RES
<222> LOCATION: (18)..(18)
<223> OTHER INFORMATION: Pro or Gln
<220> FEATURE:
<221> NAME/KEY: MOD_RES
<222> LOCATION: (24)..(24)
<223> OTHER INFORMATION: Lys or Arg
<220> FEATURE:
<221> NAME/KEY: MOD_RES
<222> LOCATION: (28)..(28)
<223> OTHER INFORMATION: Asn or Ser
<220> FEATURE:
<221> NAME/KEY: MOD_RES
<222> LOCATION: (29)..(29)
<223> OTHER INFORMATION: Ile or Leu
<220> FEATURE:
<221> NAME/KEY: MOD_RES
<222> LOCATION: (31)..(31)
<223> OTHER INFORMATION: His or Tyr
<220> FEATURE:
<221> NAME/KEY: MOD_RES
<222> LOCATION: (39)..(39)
<223> OTHER INFORMATION: Glu or Asn
<220> FEATURE:
<221> NAME/KEY: MOD_RES
<222> LOCATION: (41)..(41)
<223> OTHER INFORMATION: Tyr or Phe
<220> FEATURE:
<221> NAME/KEY: MOD_RES
<222> LOCATION: (42)..(42)
<223> OTHER INFORMATION: Leu or Gln
<220> FEATURE:
<221> NAME/KEY: MOD_RES
<222> LOCATION: (44)..(44)
<223> OTHER INFORMATION: Lys or Arg
<220> FEATURE:
<221> NAME/KEY: MOD_RES
<222> LOCATION: (50)..(50)
<223> OTHER INFORMATION: Gln, Lys or Arg
<220> FEATURE:
<221> NAME/KEY: MOD_RES
<222> LOCATION: (51)..(51)
<223> OTHER INFORMATION: Leu, Val or Arg
<220> FEATURE:
<221> NAME/KEY: MOD_RES
<222> LOCATION: (60)..(60)
<223> OTHER INFORMATION: Phe or Asp
<220> FEATURE:
<221> NAME/KEY: MOD_RES
<222> LOCATION: (81)..(81)
<223> OTHER INFORMATION: Ser or Asn
<220> FEATURE:
<221> NAME/KEY: MOD_RES
<222> LOCATION: (88)..(88)
<223> OTHER INFORMATION: Leu or Val
<220> FEATURE:
<221> NAME/KEY: MOD_RES
<222> LOCATION: (92)..(92)
<223> OTHER INFORMATION: Tyr or Phe
<220> FEATURE:
<221> NAME/KEY: MOD_RES
<222> LOCATION: (94)..(94)
<223> OTHER INFORMATION: Phe or Met
<220> FEATURE:
<221> NAME/KEY: MOD_RES
<222> LOCATION: (97)..(97)
<223> OTHER INFORMATION: Ser or Thr
<220> FEATURE:
<221> NAME/KEY: MOD_RES
<222> LOCATION: (99)..(102)
<223> OTHER INFORMATION: May or may not be present
<220> FEATURE:
<221> NAME/KEY: MOD_RES
```

<222> LOCATION: (103)..(103)
<223> OTHER INFORMATION: Phe or Trp
<220> FEATURE:
<221> NAME/KEY: MOD_RES
<222> LOCATION: (105)..(105)
<223> OTHER INFORMATION: Gly, Ser or Gln
<220> FEATURE:
<221> NAME/KEY: MOD_RES
<222> LOCATION: (109)..(109)
<223> OTHER INFORMATION: Val or Leu

<400> SEQUENCE: 25

Asp Val Val Met Thr Gln Xaa Pro Leu Ser Leu Pro Val Xaa Xaa Gly
1               5                   10                  15

Xaa Xaa Ala Ser Ile Ser Cys Xaa Ser Ser Gln Xaa Xaa Val Xaa Ser
            20                  25                  30

Asp Gly Asn Thr Tyr Leu Xaa Trp Xaa Xaa Gln Xaa Pro Gly Gln Ser
        35                  40                  45

Pro Xaa Xaa Leu Ile Tyr Lys Val Ser Asn Arg Xaa Ser Gly Val Pro
    50                  55                  60

Asp Arg Phe Ser Gly Ser Gly Ser Gly Thr Asp Phe Thr Leu Lys Ile
65                  70                  75                  80

Xaa Arg Val Glu Ala Glu Asp Xaa Gly Val Tyr Xaa Cys Xaa Gln Gly
                85                  90                  95

Xaa His Val Pro Leu Thr Xaa Gly Xaa Gly Thr Lys Xaa Glu Ile Lys
            100                 105                 110

Arg

<210> SEQ ID NO 26
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 26

Asp Val Val Met Thr Gln Thr Pro Leu Ser Leu Pro Val Thr Pro Gly
1               5                   10                  15

Glu Pro Ala Ser Ile Ser Cys Lys Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 27
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 27

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Asn Ile Val His Ser
            20                  25                  30

Asp Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 28
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Asn Ile Val His Ser
            20                  25                  30

Asp Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Val Glu Ile Lys
            100                 105                 110

Arg

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Ser or Asn
<220> FEATURE:
<221> NAME/KEY: MOD_RES
<222> LOCATION: (3)..(3)
<223> OTHER INFORMATION: Gly or Ala

<400> SEQUENCE: 29

Xaa Tyr Xaa Met Asn

<210> SEQ ID NO 30
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Tyr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Tyr Gly Lys Tyr Gly Asp Tyr Tyr Ala Met Asp Tyr Trp
            100                 105                 110

Gly Gln Gly Thr Leu Val Thr Val Ser Ser
        115                 120
```

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Asn Tyr Ala Met Ser
1               5
```

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Thr Ile Tyr Ser Gly Gly Gly Tyr Thr Phe Tyr Leu Asp Ser Leu Lys
1               5                   10                  15

Gly
```

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
His Ser Tyr Pro Met Thr Thr Val Ile Thr Tyr Ala Pro Tyr Tyr Phe
```

<210> SEQ ID NO 34
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Ala Met Ser Trp Val Lys Gln Ala Pro Gly Lys Gly Leu Lys Trp Met
        35                  40                  45

Gly Thr Ile Tyr Ser Gly Gly Tyr Thr Phe Tyr Leu Asp Ser Leu
    50                  55                  60

Lys Gly Arg Phe Val Phe Ser Leu Asp Thr Ser Val Ser Thr Ala Tyr
65                  70                  75                  80

Leu Gln Ser Ser Leu Lys Ala Glu Asp Thr Ala Val Tyr Phe Cys Ala
                85                  90                  95

Arg His Ser Tyr Pro Met Thr Thr Val Ile Thr Tyr Ala Pro Tyr Tyr
            100                 105                 110

Phe Tyr Tyr Trp Gly Gln Gly Thr Leu Val Thr Val Ser Ser
        115                 120                 125
```

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Ser Ala Ser Ser Ser Val Asn Tyr Met His
1               5                   10
```

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Ser Thr Ser Asn Leu Ala Ser
1               5
```

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
His Gln Trp Asn Asn Tyr Gly Thr
```

<210> SEQ ID NO 38
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Val Asn Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Trp Asn Asn Tyr Gly Thr Phe
                85                  90                  95

Gly Gln Gly Thr Lys Val Glu Ile Lys Arg
            100                 105

<210> SEQ ID NO 39
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Val Val Met Thr Gln Thr Pro Leu Ser Leu Pro Val Thr Pro Gly
1               5                   10                  15

Glu Pro Ala Ser Ile Ser Cys Lys Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 40
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Asp Val Val Met Thr Gln Thr Pro Leu Ser Leu Pro Val Ser Leu Gly
1               5                   10                  15

Asp Gln Ala Ser Ile Ser Cys Lys Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Val Gly Val Tyr Phe Cys Phe Gln Gly
                85                  90                  95

Ser His Val Pro Leu Thr Phe Gly Gly Gly Thr Lys Leu Glu Ile Lys
            100                 105                 110

Arg
```

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Asp Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg
```

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Asp Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Val Glu Ile Lys
            100                 105                 110

Arg

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Asp Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 44
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Asp Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Phe Gln Gly
                85                  90                  95

Ser His Val Pro Leu Thr Phe Gly Gly Gly Thr Lys Leu Glu Ile Lys
            100                 105                 110

Arg

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Asp Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg

<210> SEQ ID NO 46
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ser Gly Thr Lys Leu Glu Ile Lys
            100                 105                 110

Arg

<210> SEQ ID NO 47
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
50                      55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ala Gly Thr Lys Leu Glu Leu Lys Arg
            100                 105
```

<210> SEQ ID NO 48
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Asp Ile Val Met Thr Gln Ser Pro Ser Ser Leu Ala Val Ser Thr Gly
1               5                   10                  15

Gly Thr Val Thr Leu Thr Cys Leu Ser Ser Gln Ser Leu Phe Ser Ser
                20                  25                  30

Asp Thr Asn Lys Asn Tyr Leu Asn Trp Tyr Leu Gln Lys Pro Gly Gln
            35                  40                  45

Ser Pro Lys Leu Leu Val Tyr His Ala Ser Thr Arg Leu Thr Gly Val
50                  55                      60

Pro Asp Arg Phe Ile Gly Ser Gly Ser Gly Thr Asp Phe Thr Leu Thr
65                  70                  75                  80

Ile Asn Ser Val Gln Ala Glu Asp Leu Gly Asp Tyr Tyr Cys Gln Gln
                85                  90                  95

His Phe Arg Pro Pro Phe Thr Phe Gly Arg Gly Thr Lys Leu Glu Ile
            100                 105                 110

Lys Arg
```

<210> SEQ ID NO 49
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Ile Val Leu Thr Gln Ser Pro Ala Ile Met Ser Ala Ser Leu Gly
1               5                   10                  15

Ala Glu Ile Thr Leu Thr Cys Ser Ala Ser Ser Val Asn Tyr Met
                20                  25                  30

His Trp Tyr Gln Gln Arg Ser Gly Thr Ser Pro Lys Leu Leu Ile Tyr
            35                  40                  45

Ser Thr Ser Asn Leu Ala Ser Gly Val Pro Ser Arg Phe Ser Gly Ser
50                  55                  60
```

-continued

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Asn Asn Tyr Gly Thr Phe
                85                  90                  95

Gly Gly Gly Thr Lys Leu Glu Ile Lys Arg
            100                 105

<210> SEQ ID NO 50
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Asn Val Leu Thr Gln Ser Pro Ala Ile Leu Ala Ala Ser Leu Gly
1               5                   10                  15

Gln Lys Val Thr Met Thr Cys Ser Ala Ser Ser Ser Val Ser Ser Gly
                20                  25                  30

Tyr Leu His Trp Tyr Gln Gln Lys Ser Gly Ala Ser Pro Lys Pro Leu
            35                  40                  45

Ile His Arg Thr Ser Asn Leu Ala Ser Gly Val Pro Pro Arg Phe Ser
        50                  55                  60

Gly Ser Gly Ser Gly Thr Ser Tyr Ser Leu Ser Ile Ser Ser Val Glu
65                  70                  75                  80

Ala Glu Asp Asp Ala Thr Tyr Tyr Cys Gln Gln Trp Ser Gly Phe Pro
                85                  90                  95

Phe Thr Phe Gly Ser Gly Thr Lys Leu Glu Ile Lys Arg
            100                 105

<210> SEQ ID NO 51
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Asn Val Ser Thr Ser
                20                  25                  30

Ser Tyr Ser His Met His Trp Ser Gln Gln Lys Pro Gly Gln Pro Pro
            35                  40                  45

Lys Leu Leu Ile Lys Tyr Ala Ser Asn Leu Asp Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ile Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

<210> SEQ ID NO 52
<211> LENGTH: 112
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 52

Asp Ile Val Met Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
            20                  25                  30

Ser Tyr Ser His Met His Trp Tyr Gln Gln Lys Pro Gly Gln Pro Pro
        35                  40                  45

Lys Leu Leu Ile Arg Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Ile Tyr Tyr Cys Gln His Ser Trp
                85                  90                  95

Glu Leu Pro Tyr Thr Phe Gly Gly Gly Thr Lys Leu Glu Ile Lys Arg
            100                 105                 110

<210> SEQ ID NO 53
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Asp Ile Val Leu Thr Gln Phe Pro Ala Ser Leu Pro Val Ser Leu Gly
1               5                   10                  15

Gln Arg Ala Thr Ile Ser Cys Arg Ala Ser Gln Ser Val Ser Thr Ser
            20                  25                  30

Ser Tyr Ser His Met His Trp Tyr Gln Gln Lys Pro Gly Gln Pro Pro
        35                  40                  45

Lys Leu Leu Ile Thr Tyr Ala Ser Asn Leu Asp Ser Gly Val Pro Ala
    50                  55                  60

Arg Ile Ser Gly Ser Gly Ser Gly Thr Asp Phe Thr Leu Asn Ile His
65                  70                  75                  80

Pro Val Glu Glu Glu Asp Thr Ala Thr Tyr Tyr Cys His His Ser Trp
                85                  90                  95

Glu Leu Pro Tyr Thr Phe Gly Gly Gly Thr Lys Leu Glu Ile Lys Arg
            100                 105                 110

<210> SEQ ID NO 54
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 54

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Lys Asp Tyr Gly Lys Tyr Gly Asp Tyr Tyr Ala Met Asp Tyr Trp
            100                 105                 110

Gly Gln Gly Thr Ser Val Thr Val Ser Ser
            115                 120

<210> SEQ ID NO 55
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Leu Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Thr Leu Lys Asn Glu Asp Met Ala Thr Tyr Phe Cys
                85                  90                  95

Ala Arg Asp Thr Ala Met Asp Tyr Ala Met Ala Tyr Trp Gly Gln Gly
            100                 105                 110

Thr Ser Val Thr Val Ser Ser
        115

<210> SEQ ID NO 56
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Lys Leu Val Asp Ser Gly Gly Gly Leu Val Gln Pro Gly Asp
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Gly Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Asp Leu Arg Ala Glu Asp Thr Ala Ile Tyr
                85                  90                  95

Tyr Cys Val Arg Asp Ala Gly Tyr Gly Tyr Trp Tyr Phe Asp Val Trp

```
                   100                 105                 110

Gly Ala Gly Thr Thr Val Thr Val Ser Ser
            115                 120

<210> SEQ ID NO 57
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Ile Gln Leu Gln Glu Ser Gly Pro Ser Leu Val Lys Pro Ser Gln
 1               5                  10                  15

Ser Leu Ser Leu Thr Cys Ser Val Thr Gly Tyr Ser Ile Thr Ser Asp
            20                  25                  30

Ser Tyr Trp Asn Trp Ile Arg Gln Phe Pro Gly Lys Asn Leu Val Trp
        35                  40                  45

Met Gly Tyr Ile Ser Tyr Arg Gly Ser Thr Asn Tyr Asn Pro Ser Leu
    50                  55                  60

Lys Ser Arg Ile Ser Ile Thr Arg Asp Thr Ser Arg Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Tyr Ser Gly Tyr Ser Phe Trp Tyr Phe Asp Phe Trp Gly Gln
            100                 105                 110

Gly Thr Gln Val Thr Val Ser Ser
        115                 120

<210> SEQ ID NO 58
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Thr Thr Ser
            20                  25                  30

Asn Met Gly Val Val Trp Ile Arg Gln Pro Ser Gly Lys Gly Leu Glu
        35                  40                  45

Trp Leu Leu His Ile Leu Trp Asp Asp Arg Glu Tyr Ser Asn Pro Ala
    50                  55                  60

Leu Lys Ser Arg Leu Thr Ile Ser Lys Asp Pro Phe Asn Asn Gln Val
65                  70                  75                  80

Phe Leu Lys Ile Ala Asn Val Asp Thr Ala Asp Thr Ala Thr Tyr Tyr
                85                  90                  95

Cys Ala Arg Met Ser Arg Asn Tyr Tyr Gly Ser Ser Tyr Val Met Asp
            100                 105                 110

Tyr Trp Gly Gln Gly Thr Ser Val Thr Val Ser Ser
        115                 120

<210> SEQ ID NO 59
<211> LENGTH: 123
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Thr Gly Gln Gly Leu Glu Trp Ile
        35                  40                  45

Gly Tyr Ile Asn Ser Asn Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Thr Gly Asp Tyr Tyr Gly Gly Thr Ser Tyr Trp Tyr Phe Asp Val
            100                 105                 110

Trp Gly Ala Gly Thr Thr Val Thr Val Ser Ser
        115                 120

<210> SEQ ID NO 60
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Phe Gly Asp Thr Asn Tyr Asn Gln Asn Phe
    50                  55                  60

Lys Gly Arg Ala Thr Leu Thr Val Asp Lys Ser Ser Asn Thr Ala Tyr
65                  70                  75                  80

Met Gln Leu Met Ser Leu Thr Ser Glu Asp Ser Ala Val Tyr Tyr Cys
                85                  90                  95

Ala Arg Glu Gly Ala Ala Arg Ala Lys Asn Tyr Phe Asp Tyr Trp Gly
            100                 105                 110

Gln Gly Thr Thr Leu Thr Val Ser Ser
        115                 120

<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Gln Gln Ser Gly Pro Glu Leu Glu Thr Pro Gly Ala
1               5                   10                  15

```
Ser Val Lys Ile Ser Cys Lys Ala Ser Gly Tyr Ser Phe Thr Gly Tyr
            20                  25                  30

Asn Met Asn Trp Val Lys Gln Thr Asn Gly Lys Ser Leu Glu Trp Ile
        35                  40                  45

Gly Asn Ile Asp Pro Tyr Phe Gly Asp Ala Asn Tyr Asn Arg Lys Phe
50                  55                  60

Lys Gly Lys Ala Thr Leu Thr Val Asp Lys Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Lys Glu Gly Ala Ala Arg Ala Lys Asn Tyr Phe Asp Tyr Trp Gly
            100                 105                 110

Gln Gly Thr Thr Leu Thr Val Ser Ser
            115                 120
```

<210> SEQ ID NO 62
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Arg Gln Thr Asn Gly Lys Ser Leu Glu Trp Ile
        35                  40                  45

Gly His Ile Asp Pro Tyr Tyr Gly Asp Ala Thr Tyr Arg Gln Lys Phe
50                  55                  60

Lys Gly Lys Ala Thr Leu Thr Val Asp Lys Ser Ser Asn Thr Ala Tyr
65                  70                  75                  80

Met Gln Leu Lys Ser Leu Thr Ser Glu Asp Ser Ala Val Tyr Phe Cys
                85                  90                  95

Ala Arg Glu Gly Ala Ala Arg Ala Arg Asn Tyr Phe Asp Tyr Trp Gly
            100                 105                 110

Gln Gly Thr Thr Leu Thr Val Ser Ser
            115                 120
```

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Asp Glu Val Asp
1
```

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Ile Asn Thr Asn Thr Gly Asn Pro Thr Tyr Ala Gln Gly Phe Thr
1               5                   10                  15

Gln

<210> SEQ ID NO 65
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (14)..(14)
<223> OTHER INFORMATION: Thr or Ser
<220> FEATURE:
<221> NAME/KEY: MOD_RES
<222> LOCATION: (15)..(15)
<223> OTHER INFORMATION: Pro or Leu
<220> FEATURE:
<221> NAME/KEY: MOD_RES
<222> LOCATION: (17)..(17)
<223> OTHER INFORMATION: Glu, Asp or Gln
<220> FEATURE:
<221> NAME/KEY: MOD_RES
<222> LOCATION: (18)..(18)
<223> OTHER INFORMATION: Pro or Gln
<220> FEATURE:
<221> NAME/KEY: MOD_RES
<222> LOCATION: (24)..(24)
<223> OTHER INFORMATION: Lys or Arg
<220> FEATURE:
<221> NAME/KEY: MOD_RES
<222> LOCATION: (28)..(28)
<223> OTHER INFORMATION: Asn or Ser
<220> FEATURE:
<221> NAME/KEY: MOD_RES
<222> LOCATION: (29)..(29)
<223> OTHER INFORMATION: Ile or Leu
<220> FEATURE:
<221> NAME/KEY: MOD_RES
<222> LOCATION: (31)..(31)
<223> OTHER INFORMATION: His or Tyr
<220> FEATURE:
<221> NAME/KEY: MOD_RES
<222> LOCATION: (33)..(33)
<223> OTHER INFORMATION: Asp or Asn
<220> FEATURE:
<221> NAME/KEY: MOD_RES
<222> LOCATION: (39)..(39)
<223> OTHER INFORMATION: Glu, Asn or Asp
<220> FEATURE:
<221> NAME/KEY: MOD_RES
<222> LOCATION: (41)..(41)
<223> OTHER INFORMATION: Tyr or Phe
<220> FEATURE:
<221> NAME/KEY: MOD_RES
<222> LOCATION: (42)..(42)
<223> OTHER INFORMATION: Leu or Gln
<220> FEATURE:
<221> NAME/KEY: MOD_RES
<222> LOCATION: (44)..(44)
<223> OTHER INFORMATION: Lys or Arg
<220> FEATURE:
<221> NAME/KEY: MOD_RES
<222> LOCATION: (50)..(50)
<223> OTHER INFORMATION: Gln, Lys or Arg
<220> FEATURE:
<221> NAME/KEY: MOD_RES
<222> LOCATION: (51)..(51)

```
<223> OTHER INFORMATION: Leu, Val or Arg
<220> FEATURE:
<221> NAME/KEY: MOD_RES
<222> LOCATION: (60)..(60)
<223> OTHER INFORMATION: Phe or Asp
<220> FEATURE:
<221> NAME/KEY: MOD_RES
<222> LOCATION: (81)..(81)
<223> OTHER INFORMATION: Ser or Asn
<220> FEATURE:
<221> NAME/KEY: MOD_RES
<222> LOCATION: (88)..(88)
<223> OTHER INFORMATION: Leu or Val
<220> FEATURE:
<221> NAME/KEY: MOD_RES
<222> LOCATION: (92)..(92)
<223> OTHER INFORMATION: Tyr or Phe
<220> FEATURE:
<221> NAME/KEY: MOD_RES
<222> LOCATION: (94)..(94)
<223> OTHER INFORMATION: Phe or Met
<220> FEATURE:
<221> NAME/KEY: MOD_RES
<222> LOCATION: (97)..(97)
<223> OTHER INFORMATION: Ser or Thr
<220> FEATURE:
<221> NAME/KEY: MOD_RES
<222> LOCATION: (99)..(102)
<223> OTHER INFORMATION: May or may not be present
<220> FEATURE:
<221> NAME/KEY: MOD_RES
<222> LOCATION: (103)..(103)
<223> OTHER INFORMATION: Phe or Trp
<220> FEATURE:
<221> NAME/KEY: MOD_RES
<222> LOCATION: (105)..(105)
<223> OTHER INFORMATION: Gly, Ser or Gln
<220> FEATURE:
<221> NAME/KEY: MOD_RES
<222> LOCATION: (109)..(109)
<223> OTHER INFORMATION: Val or Leu

<400> SEQUENCE: 65

Asp Val Val Met Thr Gln Xaa Pro Leu Ser Leu Pro Val Xaa Xaa Gly
1               5                   10                  15

Xaa Xaa Ala Ser Ile Ser Cys Xaa Ser Ser Gln Xaa Xaa Val Xaa Ser
            20                  25                  30

Xaa Gly Asn Thr Tyr Leu Xaa Trp Xaa Xaa Gln Xaa Pro Gly Gln Ser
        35                  40                  45

Pro Xaa Xaa Leu Ile Tyr Lys Val Ser Asn Arg Xaa Ser Gly Val Pro
    50                  55                  60

Asp Arg Phe Ser Gly Ser Gly Ser Gly Thr Asp Phe Thr Leu Lys Ile
65                  70                  75                  80

Xaa Arg Val Glu Ala Glu Asp Xaa Gly Val Tyr Xaa Cys Xaa Gln Gly
                85                  90                  95

Xaa His Val Pro Leu Thr Xaa Gly Xaa Gly Thr Lys Xaa Glu Ile Lys
            100                 105                 110

Arg

<210> SEQ ID NO 66
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Val Val Met Thr Gln Thr Pro Leu Ser Leu Pro Val Ser Leu Gly
```

-continued

```
1               5                   10                  15
Asp Gln Ala Ser Ile Ser Cys Lys Ser Ser Gln Asn Ile Val His Ser
                20                  25                  30

Asp Gly Asn Thr Tyr Leu Glu Trp Tyr Leu Gln Lys Pro Gly Gln Ser
            35                  40                  45

Pro Lys Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Gly Gly Thr Lys Val Glu Ile Lys
                100                 105                 110

Arg
```

<210> SEQ ID NO 67
<211> LENGTH: 106
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 67

```
Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Ser Val Asn Tyr Met
                20                  25                  30

His Trp Tyr Gln Gln Lys Pro Gly Lys Ala Pro Lys Leu Leu Ile Tyr
            35                  40                  45

Ser Thr Ser Asn Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Trp Asn Asn Tyr Gly Thr Phe
                85                  90                  95

Gly Gln Gly Thr Lys Val Glu Ile Lys Arg
                100                 105
```

<210> SEQ ID NO 68
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 68

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Leu Tyr
                20                  25                  30

Gly Met Asn Trp Val Lys Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80
```

-continued

```
Leu Gln Ile Ser Ser Leu Lys Ala Glu Asp Thr Ala Val Tyr Phe Cys
                85                  90                  95

Ala Arg Asp Thr Ala Met Asp Tyr Ala Met Ala Tyr Trp Gly Gln Gly
            100                 105                 110

Thr Leu Val Thr Val Ser Ser
        115

<210> SEQ ID NO 69
<211> LENGTH: 98
<212> TYPE: PRT
<213> ORGANISM: Homo sapiens

<400> SEQUENCE: 69

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg

<210> SEQ ID NO 70
<211> LENGTH: 119
<212> TYPE: PRT
<213> ORGANISM: Mus musculus

<400> SEQUENCE: 70

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Leu Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Thr Leu Lys Asn Glu Asp Met Ala Thr Tyr Phe Cys
                85                  90                  95

Ala Arg Asp Thr Ala Met Asp Tyr Ala Met Ala Tyr Trp Gly Gln Gly
            100                 105                 110

Thr Ser Val Thr Val Ser Ser
        115

<210> SEQ ID NO 71
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 71

Asp Val Val Met Thr Gln Thr Pro Leu Ser Leu Pro Val Ser Leu Gly
1               5                   10                  15

Asp Gln Ala Ser Ile Ser Cys Lys Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Gly Gly Thr Lys Leu Glu Ile Lys
            100                 105                 110

Arg

<210> SEQ ID NO 72
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Val Val Met Thr Gln Thr Pro Leu Ser Leu Pro Val Ser Leu Gly
1               5                   10                  15

Asp Gln Ala Ser Ile Ser Cys Lys Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Phe Gln Gly
                85                  90                  95

Ser His Val Pro Leu Thr Phe Gly Gly Gly Thr Lys Leu Glu Ile Lys
            100                 105                 110

Arg

<210> SEQ ID NO 73
<211> LENGTH: 109
<212> TYPE: PRT
<213> ORGANISM: Homo sapiens

<400> SEQUENCE: 73

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Gly Gly Gly Thr Lys Leu Glu Ile Lys Arg
            100                 105

<210> SEQ ID NO 74
<211> LENGTH: 114
<212> TYPE: PRT
<213> ORGANISM: Mus musculus

<400> SEQUENCE: 74

Asp Val Leu Met Thr Gln Thr Pro Leu Ser Leu Pro Val Ser Leu Gly
 1               5                  10                  15

Asp Gln Ala Ser Ile Ser Cys Lys Ser Ser Gln Asn Ile Val His
                 20                  25                  30

Ser Asp Gly Asn Thr Tyr Leu Glu Trp Tyr Leu Gln Lys Pro Gly Gln
             35                  40                  45

Ser Pro Lys Leu Leu Ile Tyr Lys Val Ser Asn Arg Phe Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Leu Gly Val Tyr Tyr Cys Phe Gln
                 85                  90                  95

Gly Ser His Val Pro Leu Thr Phe Gly Ser Gly Thr Lys Leu Glu Ile
            100                 105                 110

Lys Arg

<210> SEQ ID NO 75
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Val Val Met Thr Gln Ser Pro Leu Ser Leu Pro Val Thr Leu Gly
 1               5                  10                  15

Glu Pro Ala Ser Ile Ser Cys Lys Ser Ser Gln Ser Leu Val His Ser
                 20                  25                  30

Asp Gly Asn Thr Tyr Leu Glu Trp Phe Leu Gln Lys Pro Gly Gln Ser
             35                  40                  45

Pro Gln Leu Leu Ile Leu Lys Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gly Gly Thr Lys Val Glu Ile Lys
            100                 105                 110

Arg

<210> SEQ ID NO 76
<211> LENGTH: 109
<212> TYPE: PRT
<213> ORGANISM: Homo sapiens
```

-continued

<400> SEQUENCE: 76

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Phe Gly Gly Gly Thr Lys Val Glu Ile Lys Arg
            100                 105

<210> SEQ ID NO 77
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Asn Met Gly Val Val Trp Ile Arg Gln Pro Pro Gly Lys Ala Leu Glu
        35                  40                  45

Trp Leu Ala His Ile Leu Trp Asp Asp Arg Glu Tyr Ser Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Ser Arg Asn Tyr Tyr Gly Ser Ser Tyr Val Met Asp
            100                 105                 110

Tyr Trp Gly Thr Leu Val Thr Val Ser Ser
        115                 120

<210> SEQ ID NO 78
<211> LENGTH: 95
<212> TYPE: PRT
<213> ORGANISM: Homo sapiens

<400> SEQUENCE: 78

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

-continued

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro
                 85                  90                  95

<210> SEQ ID NO 79
<211> LENGTH: 99
<212> TYPE: PRT
<213> ORGANISM: Homo sapiens

<400> SEQUENCE: 79

Gln Val Thr Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Met Arg Val Ser Trp Ile Arg Gln Pro Pro Gly Lys Ala Leu Glu
             35                  40                  45

Trp Leu Ala Arg Ile Asp Trp Asp Asp Asp Lys Tyr Tyr Ser Thr Ser
         50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg
```